United States Patent
Wesselmann et al.

(10) Patent No.: US 9,949,817 B2
(45) Date of Patent: Apr. 24, 2018

(54) RELEASE DEVICE FOR DETACHING A MEDICAL IMPLANT FROM AN INSERTION DEVICE AND AN INSERTION DEVICE COMPRISING A RELEASE DEVICE

(71) Applicant: BIOTRONIK AG, Buelach (CH)

(72) Inventors: Matthias Wesselmann, Ruedlingen (CH); Bodo Quint, Oberglatt (CH)

(73) Assignee: BIOTRONIK AG, Buelach (CH)

( * ) Notice: Subject to any disclaimer, the term of this patent is extended or adjusted under 35 U.S.C. 154(b) by 504 days.

(21) Appl. No.: 14/177,717

(22) Filed: Feb. 11, 2014

(65) Prior Publication Data
US 2014/0243802 A1   Aug. 28, 2014

Related U.S. Application Data

(60) Provisional application No. 61/767,804, filed on Feb. 22, 2013.

(51) Int. Cl.
| | |
|---|---|
| *A61F 2/02* | (2006.01) |
| *A61F 2/24* | (2006.01) |
| *A61F 6/16* | (2006.01) |
| *A61F 2/95* | (2013.01) |
| *A61F 2/966* | (2013.01) |
| *A61M 25/00* | (2006.01) |
| *A61F 6/18* | (2006.01) |

(52) U.S. Cl.
CPC .............. *A61F 2/02* (2013.01); *A61F 2/2436* (2013.01); *A61F 2/95* (2013.01); *A61F 2/966* (2013.01); *A61F 6/18* (2013.01); *A61M 25/0043* (2013.01)

(58) Field of Classification Search
CPC ...... A61F 2002/9517; A61F 2002/9528; A61F 2002/9534
See application file for complete search history.

(56) References Cited

U.S. PATENT DOCUMENTS

| | | |
|---|---|---|
| 5,273,042 A | 12/1993 | Lynch et al. |
| 5,529,225 A | 6/1996 | Chang |
| 6,254,628 B1 | 7/2001 | Wallace et al. |

(Continued)

FOREIGN PATENT DOCUMENTS

WO   2007029242 A1   3/2007

OTHER PUBLICATIONS

EP14152380.3 European Search Report dated Jun. 14, 2014.

*Primary Examiner* — David C Eastwood
*Assistant Examiner* — Qingjun Kong
(74) *Attorney, Agent, or Firm* — Wagenknecht IP Law Group PC

(57) ABSTRACT

A release device (150, 150a, 150b) for detaching a medical implant (105) from an insertion device (110), comprising a body (10, 10a, 10b) having a proximal end (12), which during use lies furthest from a distal end (120) of the insertion device (110), and a distal end (14), which during use faces the distal end (120) of the insertion device (110), wherein at least one first actuator (16, 18) is provided between the proximal and distal ends (12, 14), wherein the at least first actuator (16, 18) can be tilted about an axis substantially perpendicularly to at least one of the insertion elements (132, 134) so as to effect a targeted relative movement in the longitudinal direction between the first and second insertion elements (132, 134) of the insertion device (110).

8 Claims, 23 Drawing Sheets

(56) References Cited

U.S. PATENT DOCUMENTS

| | | | | |
|---|---|---|---|---|
| 2008/0319524 A1* | 12/2008 | Yachia | ...................... | A61F 2/95 |
| | | | | 623/1.11 |
| 2012/0029607 A1* | 2/2012 | McHugo | ................... | A61F 2/95 |
| | | | | 623/1.11 |
| 2013/0150829 A1* | 6/2013 | Fargahi | ................. | A61B 17/00 |
| | | | | 606/1 |

* cited by examiner

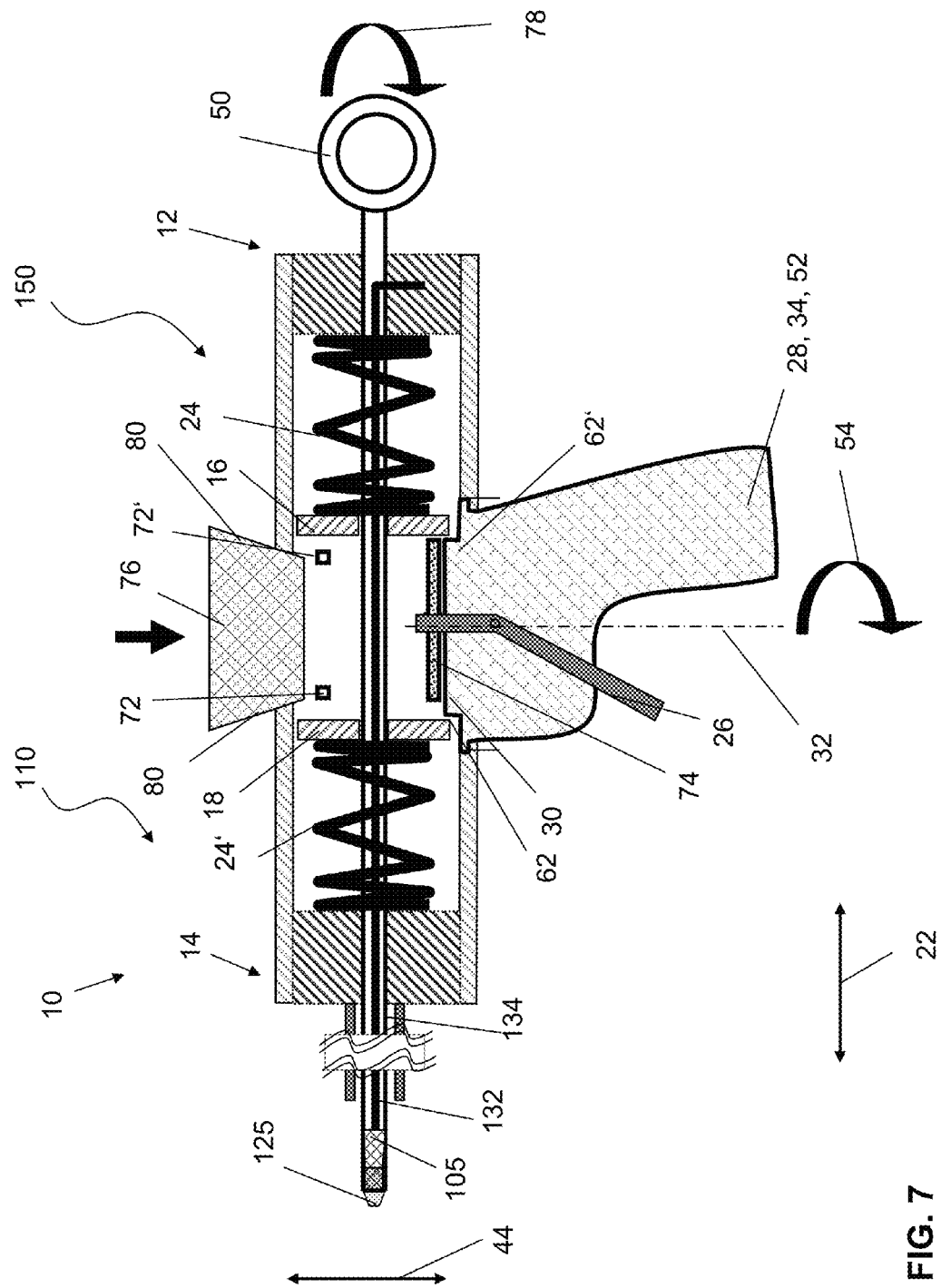

RELEASE DEVICE FOR DETACHING A MEDICAL IMPLANT FROM AN INSERTION DEVICE AND AN INSERTION DEVICE COMPRISING A RELEASE DEVICE

CROSS REFERENCE TO RELATED APPLICATIONS

This application claims benefit of priority to U.S. provisional patent application Ser. No. 61/767,804, filed Feb. 22, 2013; the content of which is herein incorporated by reference in its entirety.

TECHNICAL FIELD

The invention relates to a release device for detaching a medical implant from a catheter and to a catheter comprising a release device for releasing a medical implant for implantation in an animal and/or human body.

BACKGROUND

In medicine, implants are frequently used, which are introduced permanently, or at least for an extended period, into an animal and/or human body so as to fulfill replacement functions. These include, for example, cardiac pacemakers, brain pacemakers for patients with Parkinson's disease, cardiac implants such as heart valves or so-called septum-closure devices, cochlear implants, retina implants, dental implants, implants for joint replacement, vascular prostheses, for example insertable in the pulmonary vein, occluders, such as for the appendix, for example, or stents.

For insertion in the body, implants are connected to catheters and it must be possible to precisely place them at the site of use and release them in a defined manner. For this purpose it is known from U.S. Pat. No. 6,709,667 B1, for example, to release the implant using a sliding motion.

It is the object of the invention to provide a release device which improves the deliberate release of an implant.

It is another object to provide a corresponding insertion device.

SUMMARY

The object is achieved according to the invention by the characteristics of the independent claims. Favorable embodiments and advantages of the invention will be apparent from the remaining claims and the description.

The invention relates to a release device for detaching a medical implant from an insertion device, in which the implant can be released by a relative movement between a first and a second insertion element. The release device comprises a body, having a proximal end, which during use lies furthest from a distal end of the insertion device, and a distal end, which during use faces the distal end of the insertion device, wherein at least one first actuator is provided between the proximal and distal ends, wherein the at least first actuator can be tilted about an axis substantially perpendicularly to at least one of the insertion elements so as to effect a targeted relative movement in the longitudinal direction between the first and second insertion elements of the insertion device.

Because of the embodiment according to the invention, a release device can be provided which is designed to be operated intuitively and easily. In addition, a high release force can be introduced with a low, and more particularly a manual, operating force. Moreover, powerful movements can be transmitted by means of the actuator according to the invention, the movements reliably and homogeneously releasing the implant or allowing the same to be precisely and carefully positioned. Both a powerful and/or a well-controlled, careful release are thus made possible. This also implements a simple concept for releasing the implant. It is particularly advantageous that, by means of the embodiments according to the invention, repositioning or retraction of the partially released implant is made possible, for example in the event of mispositioning. This is in particular the case because with the device according to the invention especially high forces can be generated to press the partially expanded implant together again. The release device further provides easy handling and mounting of the implant on the insertion device, for example a catheter, in the preparatory laboratory. The simple design additionally allows the manufacturing complexity to be reduced, whereby manufacturing costs can also be kept low.

Any element that is considered suitable by a person skilled in the art can form the actuator, such as a pin, a bolt, a plate or preferably a disk or a cylinder. It is further advantageous for the at least first actuator to be formed by a block disk, whereby the at least first actuator can be designed particularly robust and durable. Alternatively, the first actuator may be embodied as a tubular or cylindrical element, thus providing an element with a reliable stability, especially a robust strength of shape. In addition, for example a non-symmetrical arrangement, or preferably a symmetrical arrangement of the at least first actuator relative to the axis is conceivable. It may also be advantageous for the least first actuator to comprise at least one passage for at least one of the insertion elements, and more particularly for an outer insertion element and/or an external shaft. This allows for a compact arrangement and a simple design option for achieving an operative connection between the at least first actuator and at least one of the insertion elements. In this context, an operative connection shall be understood to mean in particular a positive connection and/or a non-positive connection.

In addition, in this context "substantially perpendicular" shall be understood to mean a deviation of the direction of the axis toward the direction of at least one of the insertion elements relative to the perpendicular arrangement of up to 30°. In addition, "tiltable" shall be understood to mean an induced tilting movement relative to a starting position of the at least first actuator of preferably no more than 90°, advantageously of no more than 60°, and still more preferably of no more than 45°. The starting position may preferably be a perpendicular arrangement of the at least first actuator relative to the direction of at least one of the insertion elements or an arrangement that is tilted by no more than 5° to 10° relative to the perpendicular arrangement of the at least first actuator. This is especially advantageous in the case of the construction of the at least first actuator as a block disk. Alternatively, it may be also of advantage, especially when the at least one actuator is embodied as a tubular or cylindrical element, that the starting position is a parallel arrangement of the at least first actuator relative to the direction of at least one of the insertion elements or an arrangement that is tilted by no more than 5° to 10° relative to the parallel arrangement of the at least first actuator. In addition, the term "tiltable" shall be understood to mean "pivotable" or "swingable". A targeted relative movement in the longitudinal direction here constitutes in particular a movement in the axial and/or longitudinal directions. The term "to effect" here and hereinafter shall be understood to mean "to generate, cause and/or achieve". The at least first actuator can thus be disposed obliquely to the axial or longitudinal direction. In relation to at least one of the insertion elements, the perpendicular position (for the block disc construction) or the parallel position (for the tubular or cylindrical construction) of the at least first actuator constitutes a non-contact position, while the tilted or oblique position in contrast constitutes a contact position.

It is further proposed for the targeted relative movement in the longitudinal direction between the first and second insertion elements of the insertion device to occur at least by means of a non-positive connection between the at least first actuator and one of the insertion elements. Because of the non-positive connection, a proven and robust force transmission principle can be employed. An element, which transmits the advancement movement by way of a non-positive connection to one of the insertion elements, such as in particular the first actuator, is made of at least one very hard and/or rigid material, such as Inox AISI 316L or Inox AISI 306, for example. The insertion element is preferably formed by the outer insertion element. The non-positive connection can be achieved in a simple design by the tilted position of the at least first actuator and transmitted to the at least one insertion element or the external shaft.

As an alternative and/or in addition, the targeted relative movement in the longitudinal direction between the first and second insertion elements of the insertion device occurs at least by means of a positive connection between the at least first actuator and one of the insertion elements. For this purpose, preferably one material of the at least one insertion element can be adapted accordingly and comprises, for example, a material having high static friction. The at least one insertion element can thus be held in position in the tilted state relative to the at least first actuator. To this end, "high static friction" shall be understood to mean that a material can generate sufficient friction force to effect and/or induce adhesion between the at least first actuator and one of the insertion elements. This could, for example, be the case when appropriately adapting or increasing the normal force of the material. The material can be any material having sufficiently high static friction which a person skilled in the art considers suitable.

According to a further embodiment of the invention, the at least first actuator is preloaded by at least one spring element, whereby the at least first actuator can be held in a set position using a simple design. A spring element here shall be understood to mean any resilient and/or elastic element, and more particularly a spring, for example in the form of a pressure spring. According to the invention, moreover the at least first actuator can be returned to the starting position thereof by the at least one spring element. Because of this advantageous implementation, an additional restoring means for the spring element and/or the at least first actuator to be operated by a user can be dispensed with, whereby assembly can be simplified and installation space and costs can be saved. With the preferred embodiment of the spring element as a return spring, additionally a reliable component having a low weight can be used. For this purpose, it is assumed that the friction present between the outer insertion element and the body is so high that the outer insertion element remains fixed in the position thereof because of the spring element during the return movement of the at least first actuator, or does not move together with the at least one actuator. So as to prevent this under all circumstances, a blocking element may additionally be provided, which holds the outer insertion element in position. This blocking element can be formed by any element considered suitable by a person skilled in the art, such as, for example, a surface having high friction or a blocking disk, which is placed radially around the outer insertion element, for example.

In a preferred implementation, the body comprises at least one first stop for the at least first actuator. A movement of the actuator, in particular induced by the spring element, can thus be limited. The body preferably comprises at least one second stop for the actuator, wherein the first stop and the at least second stop are preferably disposed radially on top of one another, whereby the arrangement of the at least first actuator can be designed to be free of stress and load. For example, a pressure force of the return spring is homogeneously distributed over a radial extension of the at least first actuator.

It may also be advantageous for the at least first actuator to be tiltable counterclockwise so as to release the implant, whereby the tilting direction of the at least one actuator reflects a movement direction of the at least one insertion element during the release. This makes the mechanism of action intuitively understandable to the inventor. In addition, according to the invention the at least first actuator can be tilted clockwise so as to cover the implant with one of the insertion elements, whereby this induced movement is also easy to comprehend for the user. Covering the implant for this purpose shall be understood to mean covering of the implant in particular with the outer insertion element.

A release device that offers diverse and flexible use can advantageously be provided when an operating mode for the fast release of the implant is intended. This operating mode can be set using simple design measures if for the fast release of the implant the at least first actuator can be positioned substantially perpendicularly relative to at least one of the insertion elements and/or is held in a perpendicular position (for the block disc construction) or substantially parallel relative to at least one of the insertion elements and/or is held in a parallel position (for the tubular or cylindrical construction). The expressions "substantially perpendicularly" or "substantially parallel" shall be understood to mean an arrangement of the at least first actuator which deviates by no more than 5° to 10° from the perpendicular arrangement or parallel arrangement, respectively, of the at least first actuator. In the perpendicular arrangement or parallel arrangement, respectively, the non-positive connection between the at least first actuator and the at least one insertion element or the external shaft is removed, or no non-positive connection exists any longer between the at least first actuator and the at least one insertion element or the external shaft.

According to a preferred refinement, the release device comprises an operating element which can be used to induce the tilting movement of the at least first actuator and/or a targeted movement of the at least first actuator in the longitudinal direction for the targeted relative movement in the longitudinal direction between the first and second insertion elements of the insertion device. By means of the operating element, the at least first actuator can be operated easily and conveniently, notably from outside a housing of the body, inside of which the at least one actuator is disposed. The operating element can be formed by any element considered suitable by a person skilled in the art, such as a push button, a turning knob, a bracket, a lever or preferably a pivotable lever. Such an embodiment allows large forces to be transmitted to the at least first actuator in a user-friendly manner. In addition, larger working surfaces can be provided as compared to systems according to the prior art, which employ e.g. a small operating wheel. Moreover, utilizing the lever principle, the force acting on the at least one insertion element or the external shaft can be amplified via an individually pre-settable lever length of the operating element, and the extent of the release steps can also be established (see hereafter).

A pivoting movement of the operating element advantageously may have a direction opposite that of the tilting movement of the at least first actuator, whereby the operation of the operating element also becomes easy to comprehend for the user. Alternatively, the element can also be moved in the same direction, making the operation especially intuitive. The at least first actuator may preferably be in a tilted position when the operating element acts on the at least first actuator. The operating element may act on the at least first actuator directly or indirectly by means of a mediating element, such as plate, for example. By pivoting the operating element, the at least first actuator can preferably be tilted further or is preferably canted further on the outer insertion element. Because the non-positive connection between the at least first actuator and the at least one insertion element will thus always be preserved to a certain degree, or is never completely removed, and because it is assumed here that the friction present between the outer insertion element and the body is so high that the outer insertion element remains fixed in the position thereof by the spring element during the return movement of the at least first actuator, or does not move together with the at least one actuator, the targeted relative movement in the longitudinal direction between the first and second insertion elements can advantageously take place in small release steps. This is done by multiple successive actuation of the operating element.

It is further proposed for the release device to comprise a manipulating element, by which an operating mode can be set, allowing changes between modes to be easily carried out.

The manipulating element can be formed by any element considered suitable by a person skilled in the art, such as a push button, a lever, a turning knob, or a positioning slide. It may further be advantageous for the release device to comprise a manipulating element which can display an operating mode. This can reduce the assembly complexity and save space and costs, combining two functions in one component. It is further proposed for the release device to comprise an indicator element for indicating a set operating mode. The indicator element can be formed by any element considered suitable by a person skilled in the art, such as a display, scale, text field or component orientation. An indicator element shall also be understood to mean a unit comprising several identical or different indicator elements. The manipulating element and the indicator element are preferably designed integrally with one another, whereby a compact device can be achieved. Here, "integral" shall be understood to mean that the manipulating element and the indicator element are formed by the same component and/or can be separated from one another only with a loss of function of at least one of the components.

According to the invention, the body comprises at least one handle segment, creating a large working surface for handling the release device. The handle segment can be formed by any element considered suitable by a person skilled in the art, such as the housing of the body, a part of the housing, or an additionally arranged handle, such as a bow-shaped handle, for example, and preferably by a pistol grip. According to the last embodiment of the handle segment, a particularly ergonomical design can be provided, which allows the entire hand to extend around the handle segment. This is especially user-friendly because it can be done without causing fatigue for the user.

The handle segment is advantageously designed integrally with the manipulating element, whereby the operation of the manipulating element can be triggered in a streamlined manner and without time delay. According to an advantageous embodiment, the indicator element is preferably designed integrally with a rotatable handle segment, which can save space. The definition of "integral" shall be understood in each case similarly as described above. If the rotatable handle segment, the indicator element and the manipulating element are combined in one component, the user can set and detect an operating mode particularly conveniently and quickly. The rotatable handle segment is preferably formed by a non-symmetrical component, wherein the operating mode, and preferably also the movement direction, for example of the outer insertion element, can be displayed by the orientation of the handle segment, in particular intuitively for the user.

According to an advantageous embodiment, the manipulating element may comprise an effective element for changing between at least two operating modes, whereby effective transmission can be achieved. The effective element can be formed by any element considered suitable by a person skilled in the art, such as a spring, a lever, a sliding switch or notably an eccentric element. An action of the effective element can be transmitted particularly easily if it is disposed eccentrically relative to a rotational axis of the manipulating element. According to the design according to the invention, the actuation of the manipulating element, in particular the rotation thereof when designed as a rotatable handle segment, can induce various reactions, in a simple design, on different components, such as the at least first actuator and/or a further actuator, or in different regions of the body, such as a proximal and/or a distal region. To this end, the rotational axis is oriented in particular substantially perpendicularly to the longitudinal direction of the at least one insertion element and to the axis of the at least first actuator. The effective element is preferably integrally connected to the manipulating element. The definition of "integral" shall be understood similarly as described above.

It is further advantageous to provide at least one further actuator between the proximal and distal ends of the body. A special function and/or property can thus be assigned to each actuator, for example, and each actuator can be individually tailored to this function or property. This can, for example, be done by selecting a material, a dimension, such as a diameter, notably that of the passage for the at least one insertion element, a preload applied by the spring element, or another function and/or property conceivable to a person skilled in the art. All features described for the at least first actuator can also be applied to the at least further actuator.

In a further embodiment of the invention, the first actuator and the at least further actuator can be used to induce at least two different operating modes. This allows the release device to be designed so as to be operated in a particularly easy and uncomplicated manner.

Moreover, a risk of erroneous actuation of an operating mode is minimized. It is further proposed for the first actuator to induce a release of the implant and the at least further actuator to induce covering of the implant with one of the insertion elements, whereby the two primary functions of the release device can be induced by different components, thus reducing errors.

It can be further advantageous for the first actuator for the release of the implant to be disposed at the proximal end of the body and the at least further actuator for covering the implant with one of the insertion elements to be disposed at the distal end of the body. The arrangement of the two actuators in the body thus agrees with the movement direction of the at least one insertion element or the external shaft, making the operation of the release device particularly intuitive for the user. In addition, the two actuators are thus provided with sufficient space for the unimpaired tilting movements thereof.

According to a preferred refinement, the body comprises at least one receptacle for an inner insertion element for immovably fixing the inner insertion element to the body. The inner insertion element or interior shaft can thus be held or anchored securely on the body. The receptacle can be formed by any structure considered suitable by a person skilled in the art, such as a hook, a bolt, an opening, a depression, a gap or a slot, for example. It is further proposed for the receptacle to be implemented on the outer insertion element or on the exterior shaft, whereby anchoring is especially direct and immediate. For this purpose, the outer insertion element or exterior shaft must be designed such that it can absorb tensile and compression forces without bending. Particularly good fixation can advantageously be achieved by designing the receptacle as a slot. As an alternative and/or in addition, the inner exterior shaft is fixed in a further anchoring on the body and/or the housing thereof. The outer insertion element can thus be relieved of pressure. For this purpose, any connection type considered suitable by a person skilled in the art may be used, such as a non-positive, positive or bonded connection, for example by means of welding, soldering, bolting, nailing or gluing.

According to a further embodiment of the invention, the body comprises at least one passage for at least one of the insertion elements. This allows a compact arrangement, which stabilizes and protects the insertion element passing through. If the insertion device is a catheter, the respective insertion element can be an outer insertion element of the catheter.

According to a further concept of the invention, an insertion device for inserting the medical implant is provided, which can be released by a relative movement between the first and second insertion elements, comprising the release device for detaching the medical implant, comprising the body having the proximal end, which during use lies furthest from the distal end of the insertion device, and the distal end, which during use faces the distal end of the insertion device, wherein at least one first actuator is provided between the proximal and distal ends, wherein the at least first actuator can be tilted about an axis substantially perpendicularly relative to at least one of the insertion elements so as to effect a targeted relative movement in the longitudinal direction between the first and second insertion elements of the insertion device.

Because of the embodiment according to the invention, an insertion device can be provided which can be operated intuitively and easily. Moreover, a high release force can be introduced with a low, and more particularly a manual, operating force, whereby additionally powerful movements can be transmitted, by means of which the implant can be reliably and homogeneously released or precisely and carefully positioned. Both a powerful and/or a well-controlled, careful release are thus made possible. It is particularly advantageous that, by means of the embodiments according to the invention, repositioning or retraction of the partially released implant is made possible, for example in the event of mispositioning. The insertion device further provides easy handling and installation of the implant in the preparatory laboratory. The simple design additionally allows the manufacturing complexity to be reduced, whereby manufacturing costs can also be kept low.

According to an advantageous embodiment, the implant can be a self-expanding implant, whereby it can open automatically during release. Because of the self-expanding implant, an additional expansion means can be eliminated. This advantageously saves space and installation effort for the same. The insertion device can thus also be designed to be less complex. In principle, however, it would also be possible to use a balloon-expandable implant. However, the insertion device would have to be adapted accordingly, which a person skilled in the art will solve independently based on this person's knowledge in the art.

The invention will be described in more detail hereafter by way of example based on exemplary embodiments shown in the drawings. Shown are the following, in schematic illustrations:

DESCRIPTION OF THE DRAWINGS

FIG. 7 shows the release device of FIG. 1 immediately before the fast release of the implant;

DETAILED DESCRIPTION

Figure 1:
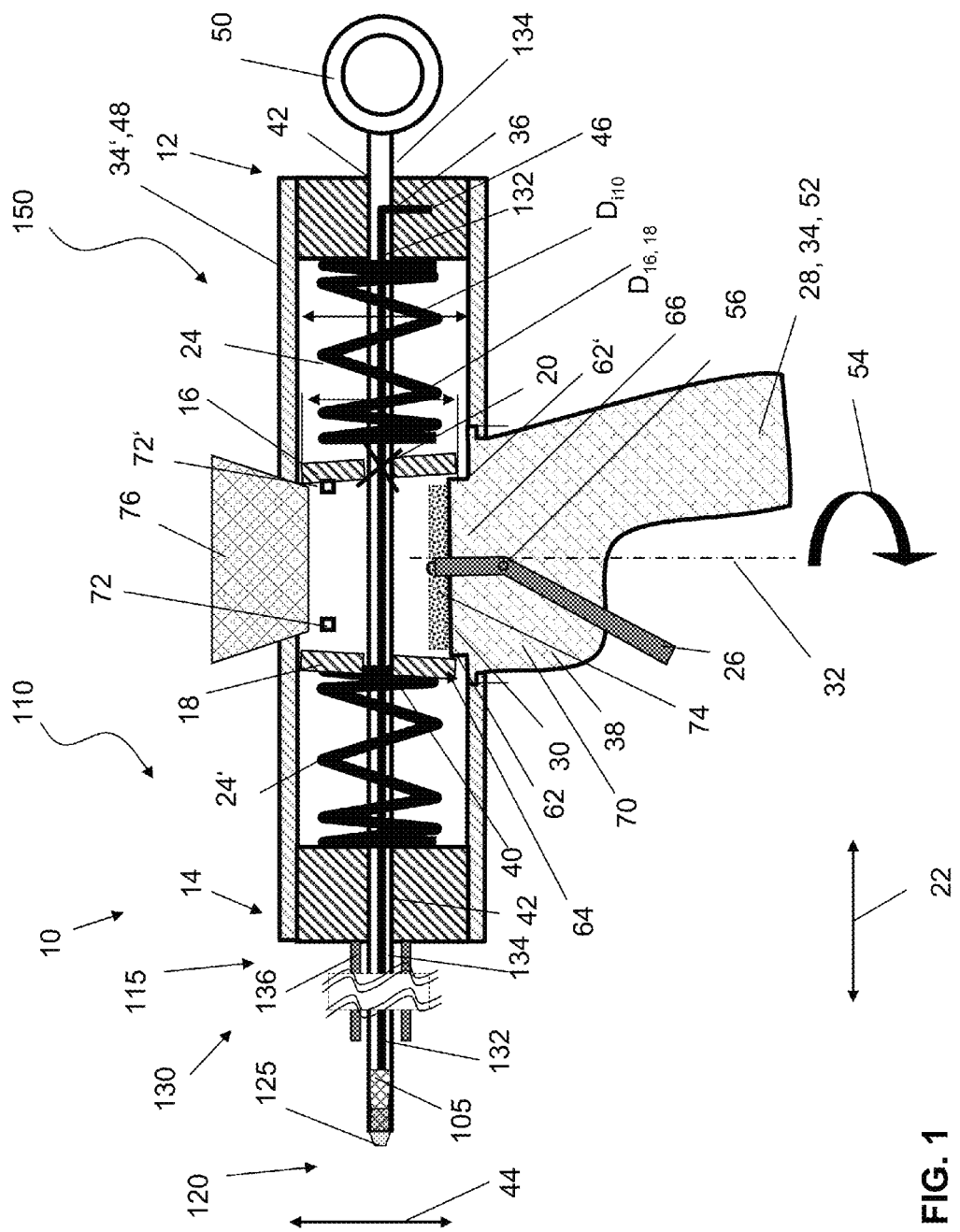
FIG. 1 is a sectional view of a favorable exemplary embodiment of an insertion device and a release device comprising a mounted implant.

In the figures, functionally equivalent or equivalently acting elements are denoted by the same reference numerals. The figures are schematic illustrations of the invention. They depict non-specific parameters of the invention. In addition, the figures only reflect typical embodiments of the invention and are not intended to limit the invention to the embodiments that are illustrated.

FIG. 1 shows a longitudinal section of a favorable exemplary embodiment of a release device 150 of an insertion device 110. The insertion device 110 is, for example, a catheter comprising a shaft region 130 having two coaxially disposed insertion elements 132, 134, for example an interior shaft (insertion element 132) and an exterior shaft (insertion element 134) which surrounds the interior shaft and can, in turn, be surrounded by an outer sheath 136. In principle, the release device can also be designed without an outer sheath. During operation, which is to say during fastening of the implant 105 to the release device 150 or during implantation, the proximal end 115 of the insertion device 110 faces a user. The implant 105 is typically positioned at the distal end 120 of the shaft region 130 between the interior shaft and exterior shaft and should be released at the implantation site in the animal or human body.

The release device 150 is used to detach the medical implant 105 from the insertion device 110. The implant 105 is disposed at the end 120 of the shaft region 130 facing away from the user, for example in the vicinity of a catheter tip 125. The implant 105 is, for example, placed around the inner insertion element 132 and is released by a relative movement between the first and second insertion elements 132, 134. To this end, the inner insertion element 132 is connected to the catheter tip 125, while the outer insertion element 134 is not.

The release device 150 comprises a body 10 having a proximal end 12, which during use lies furthest from the distal end 120 of the insertion device 110, and a distal end 14, which during use faces the distal end 120 of the insertion device 110. The body 10, or the outer insertion element 134, comprises a receptacle 36 in the form of a slot for a proximal end of the inner insertion element 132 for immovably fixing the inner insertion element 132 to the body 10. In addition, the proximal end of the inner insertion element 132 is held in the radial direction 44 after the receptacle 36 of the outer insertion element 134 in an anchoring 46 of a housing 48 of the body 10, for example positively, non-positively or by bonding. The body 10 also comprises a plurality of passages 42 for the outer insertion element 134, through which the element exits the body at the proximal end 12 of the body 10. At a proximal end of the outer insertion element 134, an operating element 50 in the form of a loop handle is formed on outside the body 10.

Figure 8A:
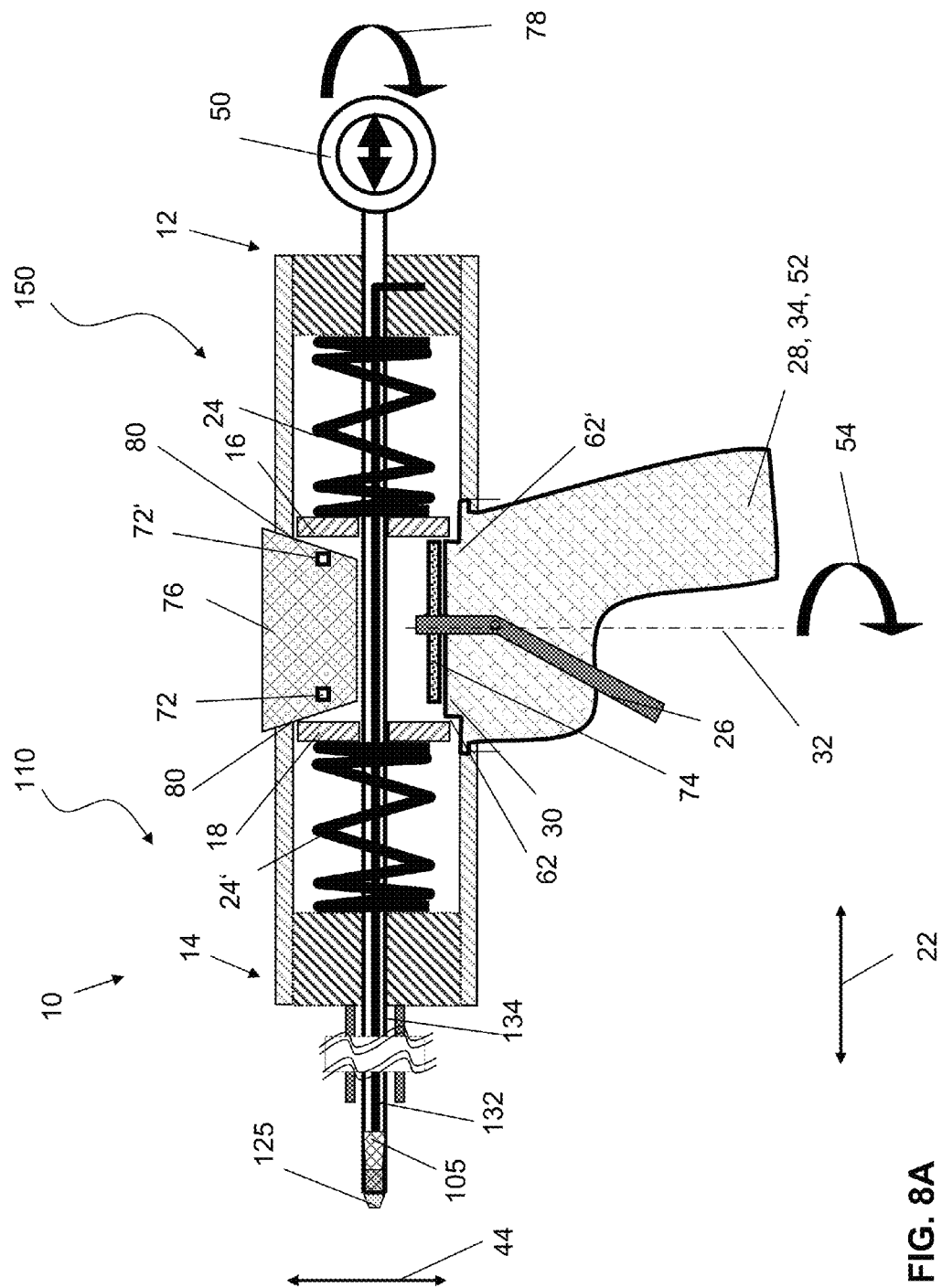
FIG. 8A shows the release device of FIG. 1 activated for the fast release of the implant.
Figure 8B:
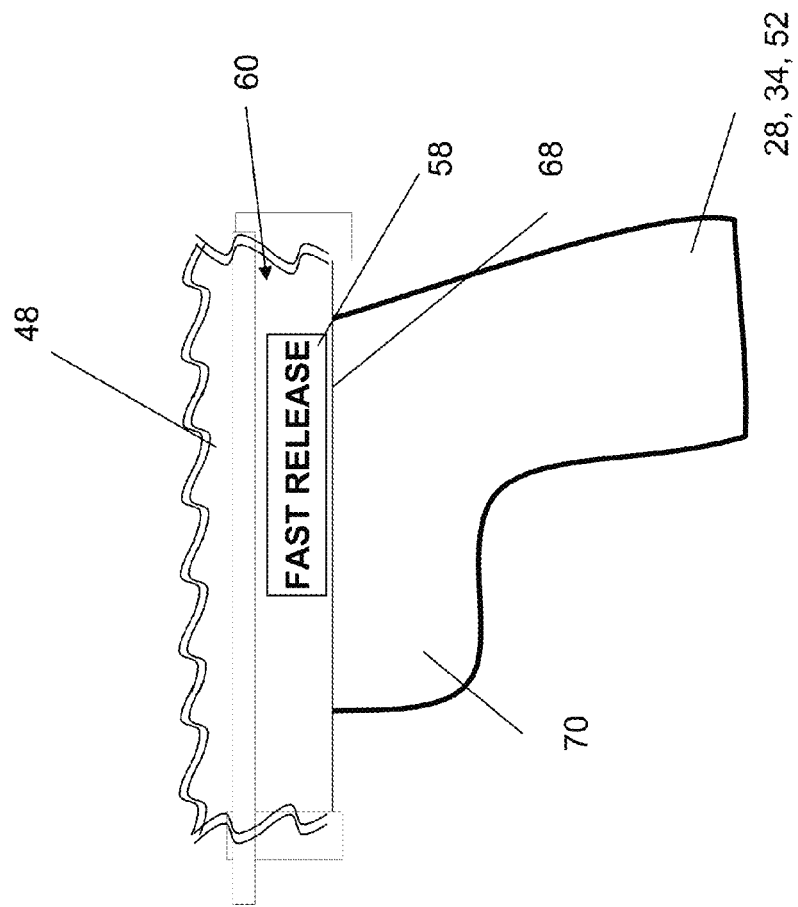
FIG. 8B is a side view of the handle segment of the release device of FIG. 1 with indication of the operating mode of the fast release of the implant.
Figure 9:
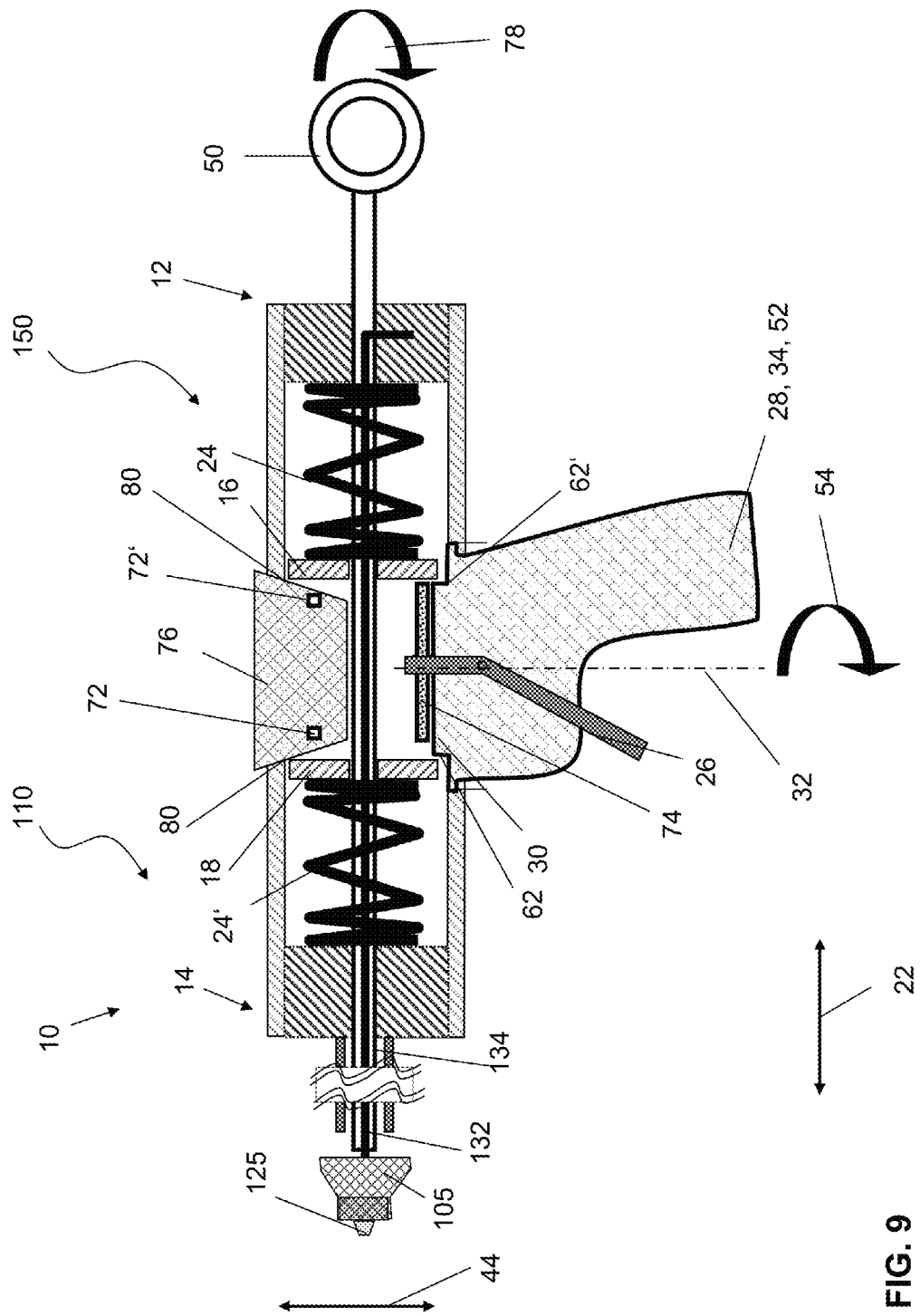
FIG. 9 shows the release device of FIG. 1 during the fast release of the implant.

In an axially central position, the body 10 comprises a handle segment 34, which is oriented substantially perpendicularly relative to the body 10, and which in a working situation, such as during implantation for example, is pointed downward relative to the body 10 and designed as a pistol grip 52. The handle segment 34 is further designed or mounted such that it can be rotated about the rotational axis 32 thereof in the circumferential direction 54 of the handle segment 34. The body 10 can be used as a second handle segment 34'. In addition, an operating element 26 in the form of a pivotable operating lever is pivotably mounted about an installation point 56 on the handle segment 34. The release device 150 moreover comprises a manipulating element 28, which can be used to set an operating mode of the release device 150 (see below). The manipulating element 28 is designed integrally with the handle segment 34 or the pistol grip 52. The release device 150 further comprises an indicator element 38 for indicating the set operating mode. The indicator element 38 is also designed integrally with the rotatable handle segment 34 or the pistol grip 52 and, depending on the operating mode, is formed by lettering 58 which denotes the operating mode and is visible in a display 60 of the housing 48 of the body 10, in accordance with the operating mode that is set (see FIGS. 2B, 4B, 8B).

Between the proximal and distal ends 12, 14 of the body 10, the body comprises two actuators 16, 18, the first actuator 16 being disposed at the proximal end 12 and the further actuator 18 being disposed at the distal end 14. Each actuator 16, 18 is formed by a block disk having a diameter $D_{16,18}$ which is selected such that the actuators 16, 18 are disposed with play for a tilting movement of the actuators 16, 18 relative to an inside diameter $D_{i10}$ of the body 10. The first and further actuators 16, 18 each have a passage 40 for the outer insertion element 134. This passage 40 extends symmetrically around a center of the actuator 16, 18, whereby the actuator 16, 18 is also disposed symmetrically relative to the outer insertion element 134. So as to effect a targeted relative movement in the longitudinal direction 22 or an axial direction between the first and second insertion elements 132, 134 of the insertion device 110, the first actuator 16 and the further actuator 18 can both be tilted about an axis 20 (see below). The axis 20 is oriented perpendicularly to the two insertion elements 132, 134 (shown only for actuator 16).

The first actuator 16 and the further actuator 18 are each preloaded by a spring element 24, 24', which extends either between the proximal end 12 of the body 10 and the actuator 16 or between the distal end 14 of the body 10 and the actuator 18 and is designed as a pressure spring. In a starting configuration, which is set before implantation, for example, the actuators 16, 18 are axially fixed in their respective axis 20 between the respective spring element 24, 24' and a stop 62, 62'. A respective stop 62, 62' points in the direction of the proximal end 12 or in the direction of the distal end 14 and is disposed in or molded on as part of a region 64 of the handle segment 34 disposed inside the body 10. In this arrangement, additionally each actuator 16, 18 is tilted around its axis 20 by the pressure of the respective spring element 24, 24° against the corresponding stop 62, 62'. The actuators 16, 18 thus effect a non-positive connection with the outer insertion element 134, whereby the same is axially fixed relative to the body 10 and the inner insertion element 132.

The first and further actuators 16, 18 can induce two different operating modes, and more specifically a release of the implant 105 can be induced by the first actuator 16 and a covering of the implant 105 with the outer insertion element 134 can be induced by the further actuator 18. The manipulating element 28 comprises an effective element 30 for changing between the two operating modes. This effective element 30 is formed by a disk 66 disposed on the manipulating element 28 or designed integrally therewith and is disposed eccentrically to the rotational axis 32 of the manipulating element 28. The stops 62, 62' are formed on the effective element 30. To provide a better understanding, the stop 62 is referred to hereinafter as a wide stop 62 and stop 62' is referred to as a narrow stop 62'.

Figure 2A:
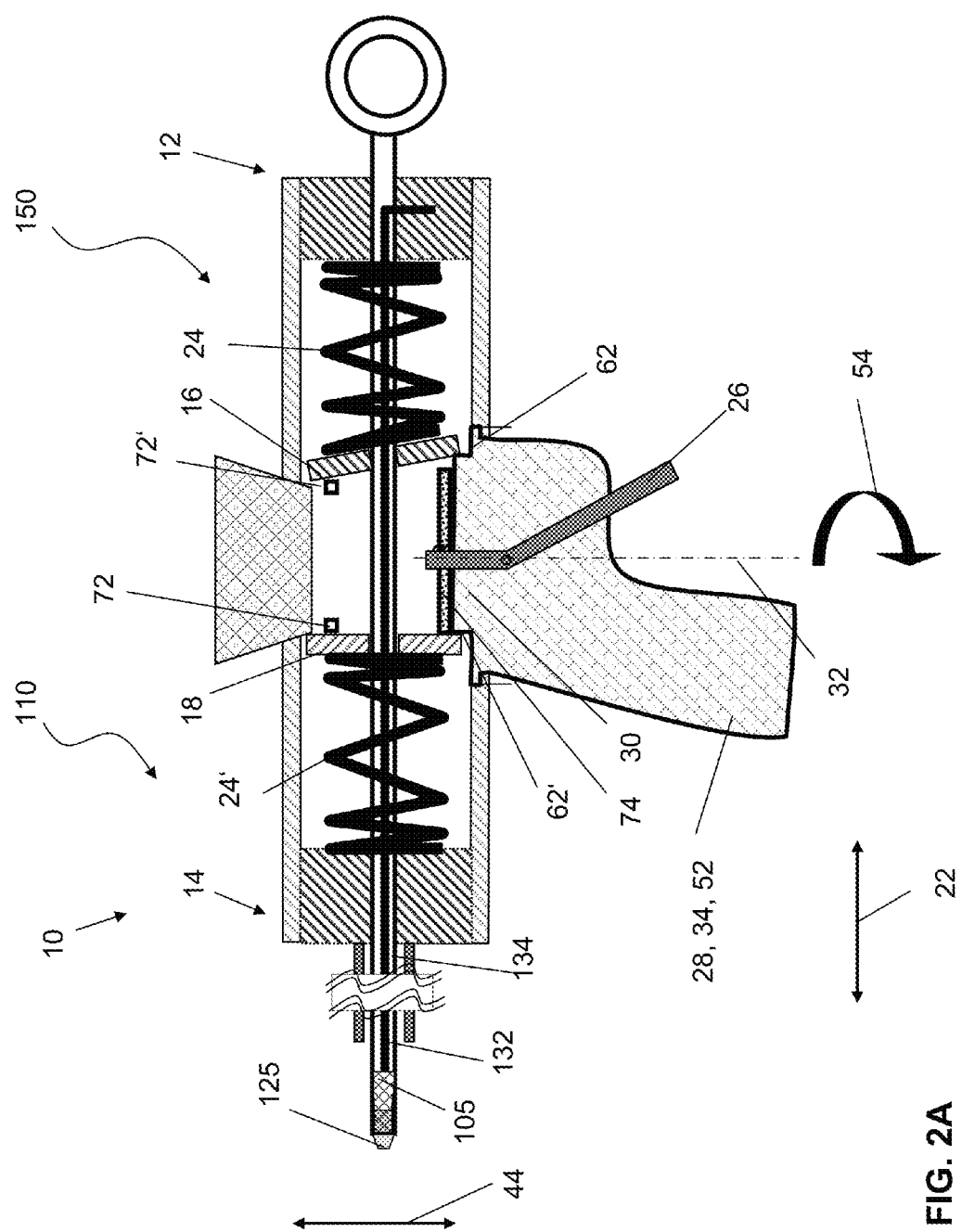
FIG. 2A shows the release device of FIG. 1 prepared for a release of the implant.
Figure 2B:
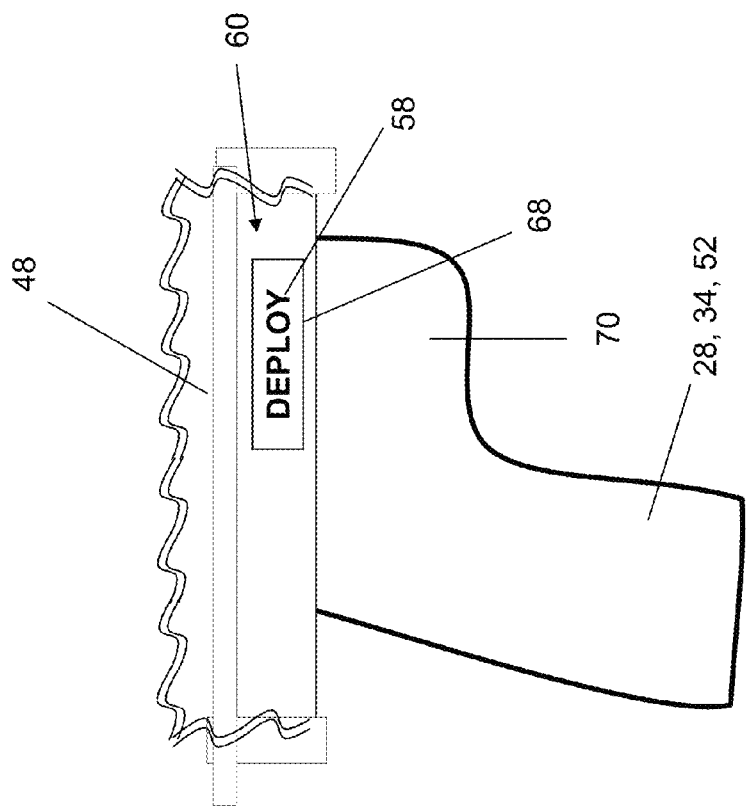
FIG. 2B is a side view of a handle segment of the release device of FIG. 1 with indication of the operating mode of the slow release of the implant.

A slow release of the implant 105 using a so-called deploy mode will now be described based on FIGS. 2A, 2B and 3. To implant the implant 105 in the body, the insertion device 110 thus prepared is inserted in the body (not shown). To release the implant 105, the manipulating element 28 or the handle segment 34 (pistol grip 52) is rotated in the circumferential direction 54 until the lettering 58 "DEPLOY" appears in the display 60 of the indicator element 38 (see FIG. 2B). This can also be the preset operating mode. The lettering 58 DEPLOY can, for example, be engraved in a wheel, which is not shown in detail here and which rotatably mounts the handle segment 34. Depending on the handle segment position, a window 68 in the housing 48 displays the corresponding lettering 58 on the wheel. The pistol grip 52 is thus also implemented as an indicator element 38 because it indicates the movement direction of the outer insertion element 134 by an orientation of the knob 70 against which a dorsum of a hand is placed, which is not shown. So as to release the implant 105, this means that the exterior shaft is moved in the direction of the proximal end 12 and the knob 70 of the handle segment 34 points in the direction of the proximal end 12.

By rotating the handle segment 34, the positions of the wide and narrow stops 62, 62' also change, the wide stop 62 now pointing in the direction of the proximal end 12 and the narrow stop 62' now pointing in the direction of the distal end 14. Because of the eccentric arrangement of the effective element 30, an axial gap (not shown) is created between the narrow stop 62' and the further actuator 18. This axial gap is now closed because of the preloading of the actuator 18 by the spring element 24' in that the spring element 24' shifts the further actuator 18 in the direction of the proximal end 12. The axial movement is carried out until the further actuator 18 strikes against the narrow stop 62'. In this release operating mode, an upper left stop 72' is provided or molded on as part of the body 10 at the same axial height as the narrow stop 62' radially above the same, with the further actuator 18 likewise striking against this stop 72'. This moves the further actuator 18 in a perpendicular position relative to the outer insertion element 134, whereby the non-positive connection between the further actuator 18 and the outer insertion element 134 is removed.

In contrast, the first actuator 16 is tilted further counterclockwise by the wide stop 62. The tilting movement is limited by an upper right stop 72. In the covering operating mode, this upper right stop 72 is provided or molded on as part of the body 10 at the same axial height as the narrow stop 62' radially above this stop 62' (see FIGS. 1 and 4). This arrangement amplifies the non-positive connection between the first actuator 16 and the outer insertion element 134.

During an actuation of the operating element 26 in this operating mode, the further actuator 18 is held in a perpendicular position relative to the outer insertion element 134 at the distal end 14 of the body 10 by the wide stop 62', so that no non-positive connection is created between the further actuator 18 and the outer insertion element 134.

Figure 3:
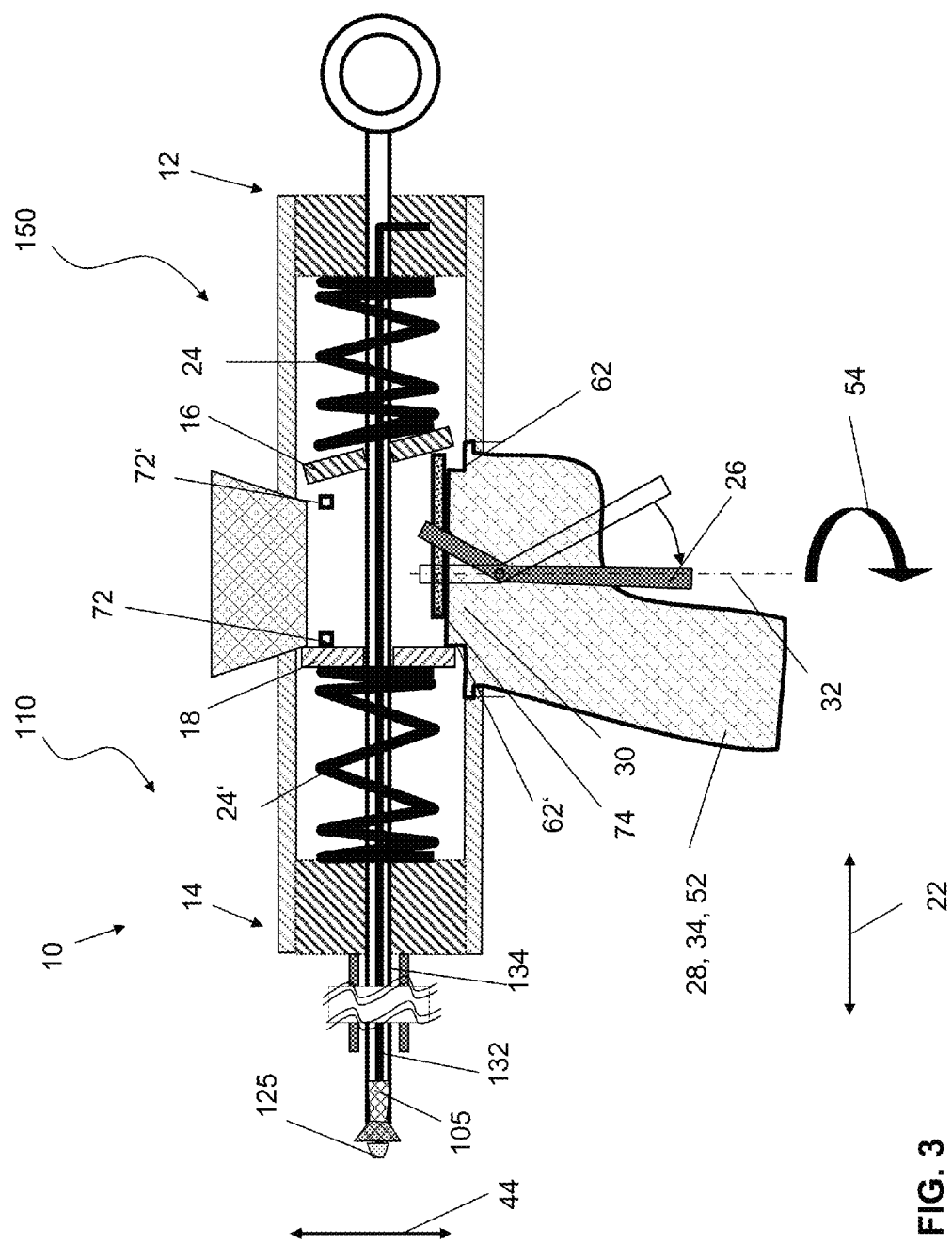
FIG. 3 shows the release device of FIG. 1 during the slow release of the implant.

As is shown in FIG. 3, the clockwise (see arrow) pivoting of the operating element 26 moves a plate 74 in the direction of the proximal end 12, the plate 74 being hinged to the operating element 26 and disposed axially displaceably parallel to the longitudinal direction 22. When the plate 74 strikes against the first actuator 16, it tilts the same further counterclockwise, whereby the first actuator 16 can be tilted counterclockwise so as to release the implant 105. The further tilting additionally increases the non-positive connection. If no further tilting is possible, the first actuator 16 is moved by the plate 74 in the longitudinal direction 22 toward the proximal end 12. Because of the non-positive connection between the first actuator 16 and the outer insertion element 134, this element 134 is also pushed in the direction of the proximal end 12.

The operating element 26 thus induces both the tilting movement and the targeted movement in the longitudinal direction 22 of the first actuator 16 for the targeted relative movement in the longitudinal direction 22 between the first and second insertion elements 132, 134, and the exterior shaft is retracted relative to the interior shaft, and thus relative to the implant 105, by the actuation of the operating element 26. The implant 105 is thus exposed and expands automatically, for example when designed as a self-expandable implant 105, such as a stent-based heart valve, and/or with the aid of a balloon. The release device 150 or the interior shaft is then retracted in the exterior shaft, and the insertion device 110 is removed from the body. The implant 105 remains fully positioned in the body (not shown).

Figure 4A:
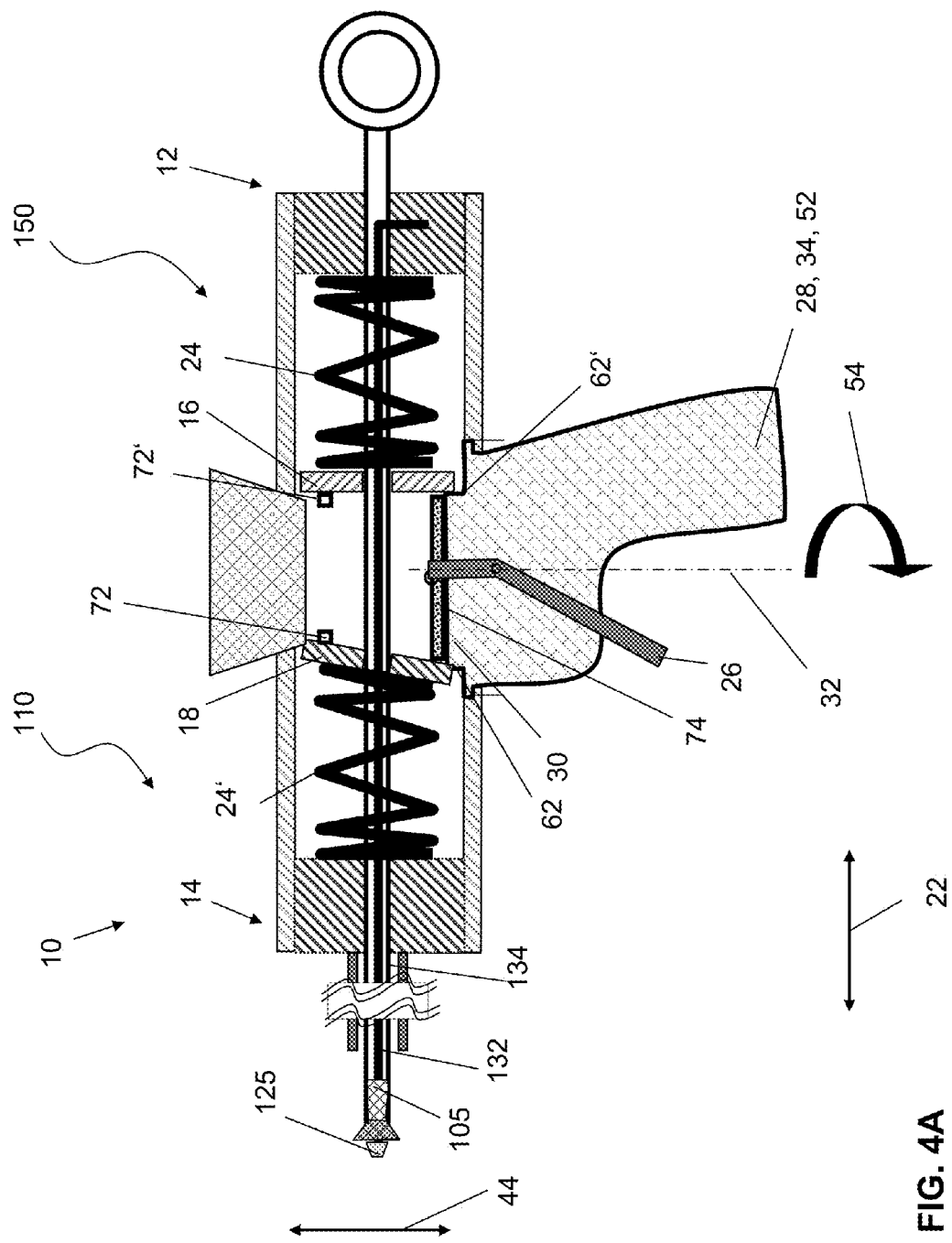
FIG. 4A shows the release device of FIG. 1 prepared for covering the implant.
Figure 4B:
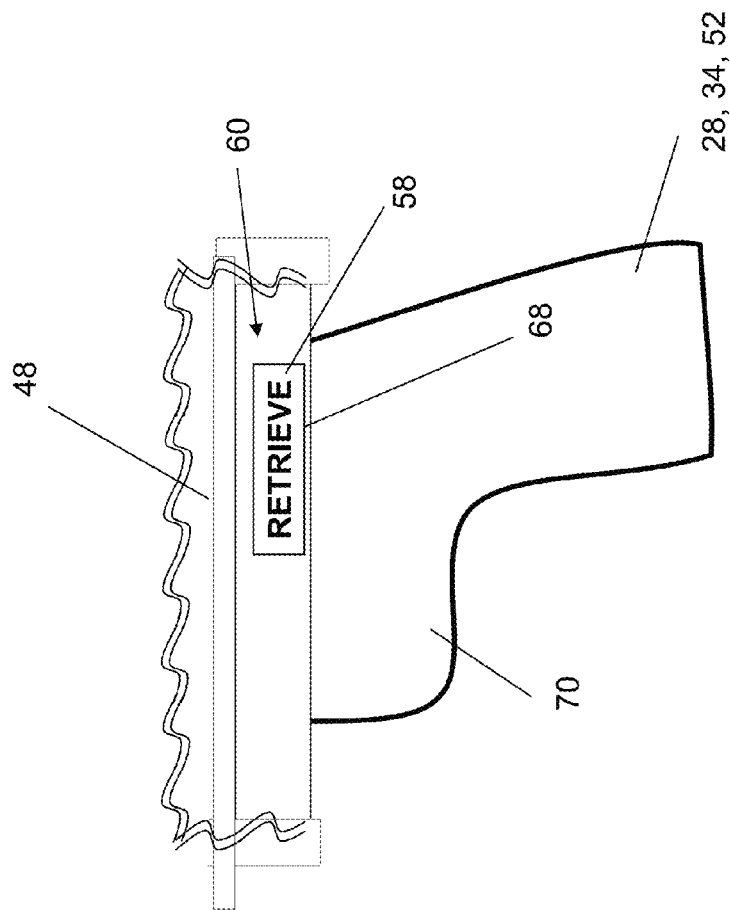
FIG. 4B is a side view of the handle segment of the release device of FIG. 1 with indication of the operating mode of the covering of the implant.
Figure 5:
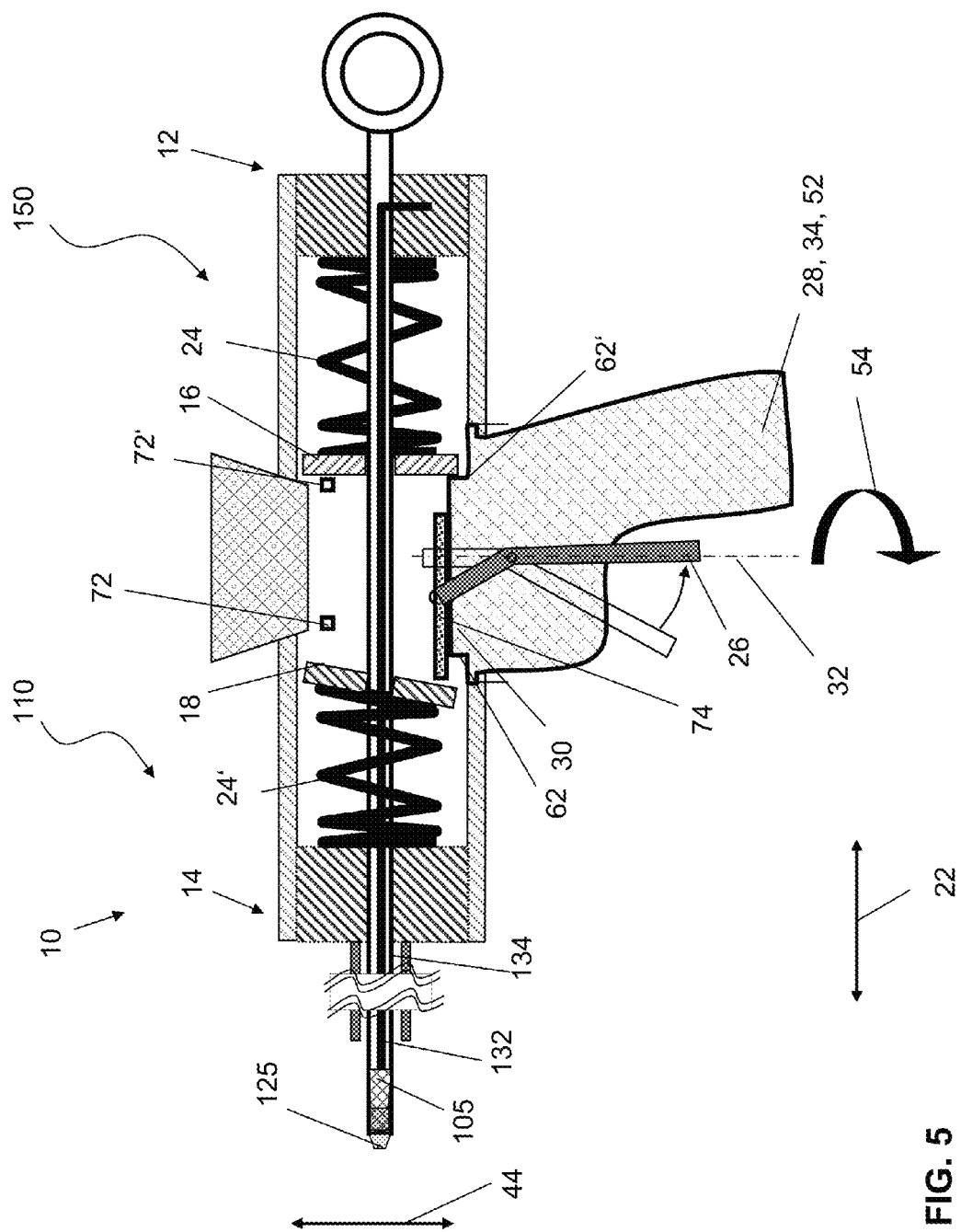
FIG. 5 shows the release device of FIG. 1 during covering of the implant.
Figure 6:
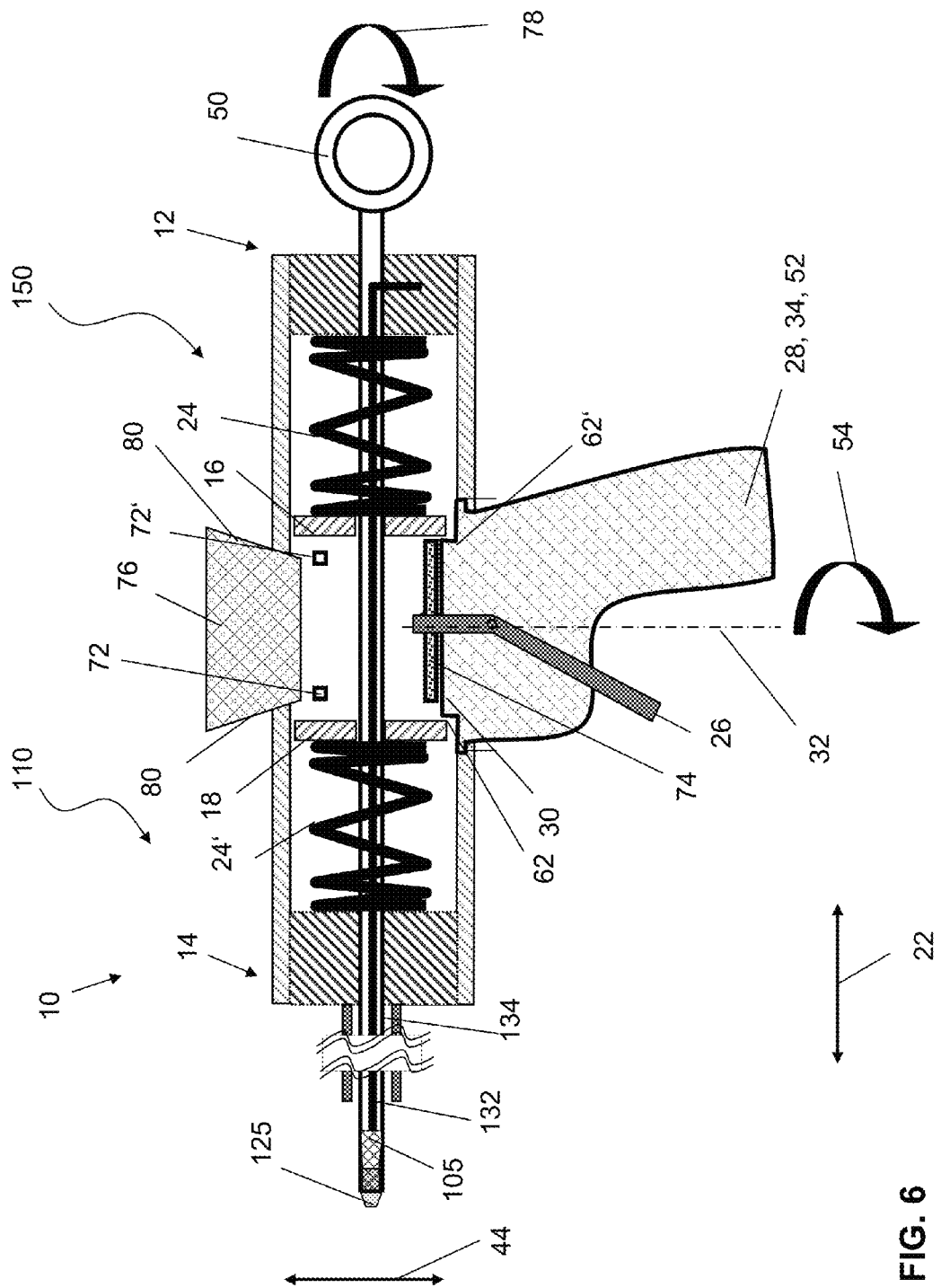
FIG. 6 shows the release device of FIG. 1 prepared for a fast release of the implant.

Based on FIGS. 4A, 4B and 5, the operating mode of covering the implant 105 with the outer insertion element 134 is described, a so-called retrieval mode. This can, for example, be used for mounting the implant 105 in the insertion device 110 or for retracting and/or re-covering the implant 105 during implantation in the event of mispositioning or a malfunction of the implant 105. The forces required to do so are significantly greater than during the release, because the, for example semi-deployed, implant 105 must be brought back to the compressed or folded small diameter. The retrieval mode is set by rotating the manipulating element 28 or the handle segment 34 (pistol grip 52) in the circumferential direction 54 until the lettering 58 "RETRIEVE" appears in the display 60 of the indicator element 38. The knob 70 thus points in the direction of the distal end 14 so as to symbolize that the outer insertion element 134 will be moved in the direction of the distal end 14 (see FIG. 4B).

In this position of the handle segment 34, the eccentric effective element 30 is disposed such that the wide stop 62 points in the direction of the distal end 14 and the narrow stop 62' points in the direction of the proximal end 12. This creates an axial gap (not shown) between the narrow stop 62' and the first actuator 16. This axial gap is closed because of the preloading of the actuator 16 by the spring element 24 in that the spring element 24 shifts the first actuator 16 in the direction of the distal end 14. The axial movement is carried out until the first actuator 16 strikes against the narrow stop 62' and the upper right stop 72. Because of the arrangement at the same axial height, the first actuator 16 is located perpendicular to the outer insertion element 134 and the non-positive connection between the first actuator 16 and the outer insertion element 134 is lifted or the first actuator 16 can thus no longer block the outer insertion element 134. In contrast, the wide stop 62 tilts the further actuator 18 clockwise until the tilting movement is limited by the upper left stop 72'. The further actuator 18 is thus canted non-positively relative to the outer insertion element 134.

If the operating element 26 is now actuated counterclockwise (see arrow), the plate 74 of the operating element 26 is moved in the direction of the distal end 14 and, after striking against the further actuator 18, tilts the same further clockwise, whereby the further actuator 18 can be tilted clockwise so as to cover the implant 105 with the outer insertion element 134. If no further tilting is possible, the plate 74 of the operating element 26 moves the canted further actuator 18 in the longitudinal direction 22 toward the distal end 14 and the further actuator 18 in turn carries the outer insertion element 134 along by way of the non-positive connection toward the distal end 14. At the catheter tip 125, this results in an advancement of the outer insertion element 134 toward the catheter tip 125. If the implant 105 is axially blocked by the inner insertion element 132, the outer insertion element 134 again slides over the implant 105 and covers the same.

If the operating element 26 is now released, the spring element 24', which also constitutes a return spring, pushes the further actuator 18 into the non-canted upright, perpendicular position and then in the longitudinal direction 22 back to the starting position against the wide and the upper left stops 62, 72', where the actuator is canted again. This process can be repeated until the outer insertion element 134 again completely covers the implant 105. The implant 105 is thus positioned in the outer insertion element 134 and the mounting is complete.

In principle, it would also be conceivable to design the release device with only one actuator, which induces both operating modes. For this purpose, for example, two operating elements would have to be provided to induce opposing tilting movements. To this end, the first operating element acts on a first side of the actuator and the second operating element acts on a second side of the actuator located opposite the first side. As an alternative, it would also be possible to provide only one operating element, which in a first position, which is at the bottom of the body, acts on a first side of the actuator and is rotated about the axis thereof for acting on a second side of the actuator located opposite the first side, and is subsequently rotated additionally in the circumferential direction of the body against an upper face of the body. In principle, this one actuator could also be rotated with the operating element so as to induce the two modes. This could, for example, be implemented with a simple design if the actuator is rigidly connected to the operating lever and/or designed integrally therewith.

FIGS. 6 to 9 show a third operating mode for a fast release of the implant 105, a so-called fast release mode. The fast release mode is activated by displacing a pressure switch 76 in the radial direction 44 (see arrow FIG. 7). To indicate the operating mode set now, the lettering 58 "FAST RELEASE" is indicated in the window 68 of the display 60 (see FIG. 8B). This can be done by a panel which is moved by the pressure switch 76 in the circumferential direction 78 of the body 10, causing the lettering 58 to appear in the window 68. In the fast release operating mode, the pressure switch 76 when depressed serves as an axial support surface 80 for the first and further actuators 16, 18 (see FIG. 8A). By the support against the pressure switch 76, the two actuators 16, 18 are brought into the perpendicular position relative to the outer insertion element 134, so that the non-positive connection is removed and the outer insertion element 134 can be moved freely. For illustration purposes, the perpendicular positions are already shown in FIGS. 6 and 7, although the actuators 16, 18 are still arranged in the canted positions there. When the actuators 16, 18 are in the perpendicular positions, the user can now pull on the operating element 50 at the proximal end of the outer insertion device 134 for a fast release of the implant 105 (see arrow FIG. 8A). This moves the outer insertion element 134 in the direction of the proximal end 12 and the implant 105 is released (see FIG. 9).

FIGS. 10 to 20 show two alternative exemplary embodiment of the body 10 or release device 150. Identical components, features and functions are denoted by the same reference numerals. However, to distinguish the exemplary embodiment of FIGS. 10 to 20 over that of FIGS. 1 to 9, the letters 'a' and 'b' has been added to the reference numerals of the components that are designed differently in the exemplary embodiment of FIGS. 10 to 20. The description below is substantially limited to these differences compared to the exemplary embodiment of FIGS. 1 to 9, wherein reference is made to the description of the exemplary embodiment in FIGS. 1 to 9 with respect to identical components, features, and functions.

FIGS. 10 to 15 show a first alternative embodiment of the body 10 and the release device 150 of FIGS. 1 to 9. The release device 150a or the body 10a of FIGS. 10 to 15 differs from the body 10 and the release device 150 of FIGS. 1 to 9 in that, for setting an operating mode, the body 10a comprises a manipulating element 28a which is designed as an axially displaceable selector switch. The manipulating element 28a or the selector switch comprises two limbs 82, 82' projecting in the radial direction 44 into a housing 48 of the body 10a, wherein limb 82 is disposed in the direction of a proximal end 12 and limb 82' is disposed in the direction of a distal end 14 of the body 10a. A first actuator 16 is disposed proximally of the limb 82 and a further actuator 18 is disposed distally of the limb 82'. For establishing contact with the actuators 16, 18 and/or for limiting a movement of the actuators 16, 18 in a longitudinal direction 22, each limb 82, 82' has two stops 62, 62', 72, 72' disposed radially on top of one another at the side of the limb pointing toward the respective actuator 16, 18.

In addition, the release device 150a includes an operating element 26a, which is formed by a pivotable operating lever which engages in the housing 48 and completely spans an inside diameter $D_{i10}$ of the body 10 in the radial direction 44. Moreover, a pivot axis 84 of the operating element 26a is oriented parallel to an axis 20 of the actuator 16, 18 and is located at the same height as an outer insertion element 134 in the radial direction 44. A lower web 86 and an upper web 86' are hinged to the operating element 26a for establishing contact with the actuators 16, 18, each web 86, 86' being axially guided on one of two radially opposing inner walls 88 of the housing 48. For this purpose, the limbs 82, 82' of the manipulating element 28a must comprise openings, which are not shown in detail here, for the webs 86, 86' to pass through.

The body 10a or the housing 48 further comprises an indicator element 38a for indicating a set operating mode. To this end, the indicator element 38a is formed by a text field having three letterings 58 denoting the operating modes. The text field is attached to the housing 48 so as to be visible to a user. For better illustration, FIGS. 10 to 15 show the field above the representation of the body 10a.

Figure 10:
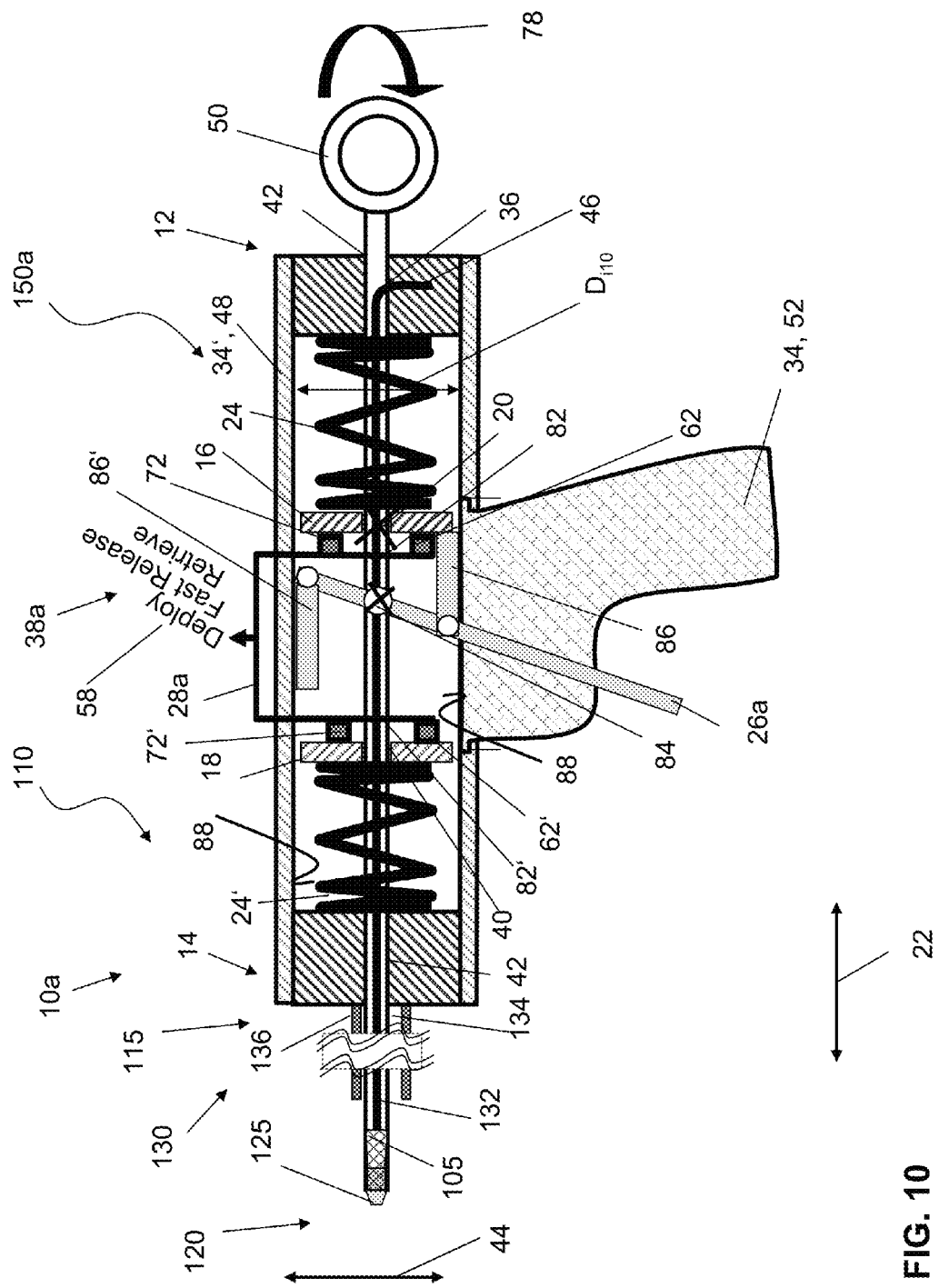
FIG. 10 is a first alternative release device prepared for a slow release of an implant.
Figure 11:
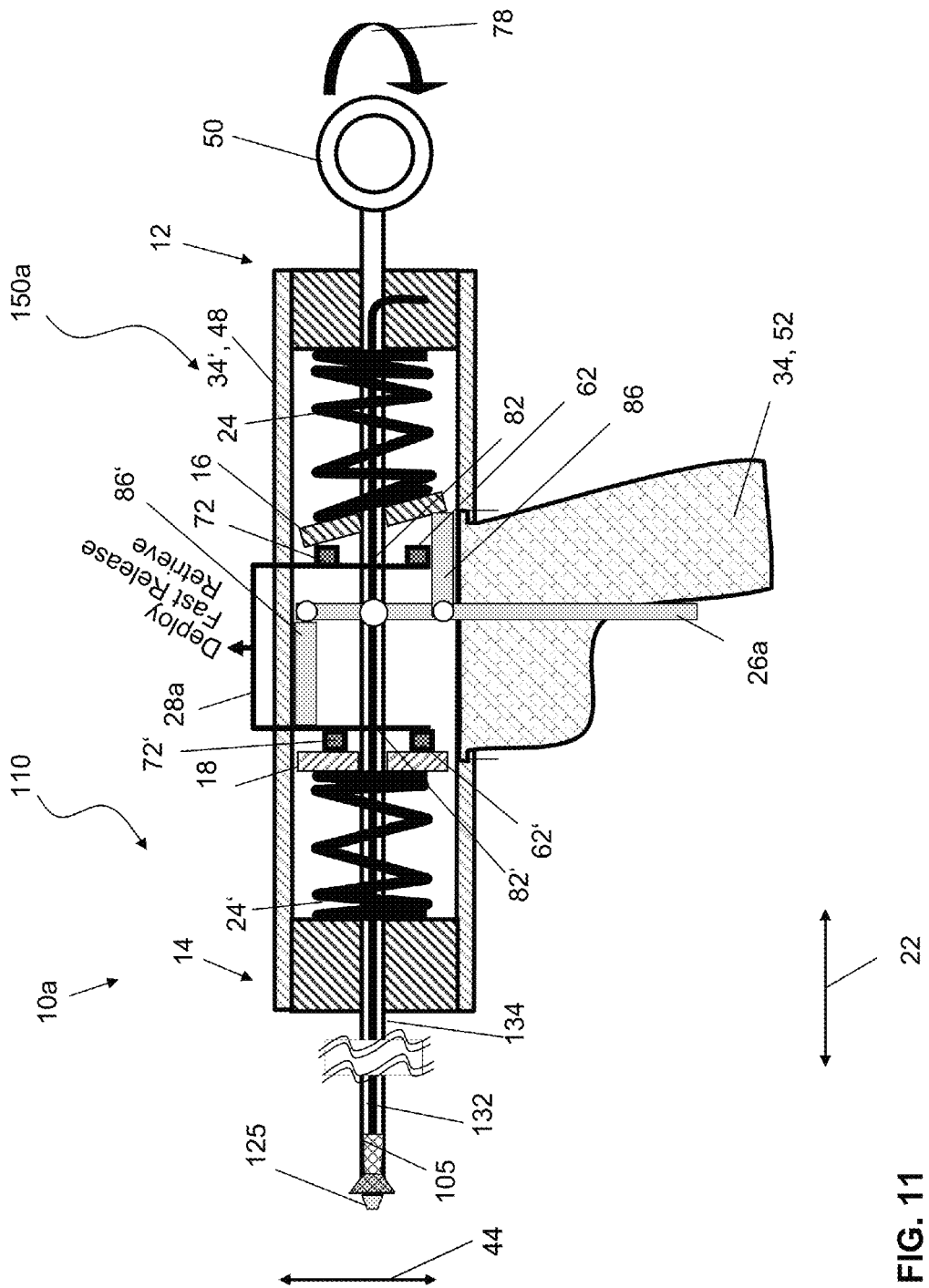
FIG. 11 shows the release device of FIG. 9 during the slow release of the implant.

With reference to FIGS. 10 and 11, hereafter a slow release of an implant 105 will be described based on a deploy mode. The deploy mode is activated by an axial displacement of the manipulating element 28a or of the selector switch in the direction of the distal end 14. This is indicated to a user by an arrow directed to the lettering 58 "DEPLOY". The stops 62', 72' of the limb 82' are axially displaced in the housing 48 such that the further actuator 18 is displaced in the direction of the distal end 14 so far that, during counterclockwise actuation, the upper web 86' of the operating element 26a can no longer establish contact with the further actuator 18 (see FIG. 11). The stops 62, 72 of the limb 82 for the first actuator 16 are likewise displaced in the direction of the distal end 14. As a result, the lower web 86 of the operating element 26a makes contact with the first actuator 16, tilts the same counterclockwise and thus cants the same on the outer insertion element 134 (see FIG. 10).

If the operating element 26*a* is now actuated counterclockwise, the lower web 86 shifts the canted actuator 16 in the direction of the proximal end 12 and the actuator 16 carries the insertion element 134 in the direction of the proximal end 12, again by way of a non-positive connection between the first actuator 16 and the outer insertion element 134. Due to the tilting movement of the first actuator 16 or the non-positive connection, a targeted relative movement is induced in the longitudinal direction 22 between the first and second insertion elements 132, 134. At the catheter tip 125, this results in a retraction of the outer insertion element 134 away from the catheter tip 125. If the implant 105 is axially blocked by the inner insertion element 132, the outer insertion element 134 pulls back from the implant 105 in the direction of the proximal end 12 and releases the implant 105.

Figure 12:
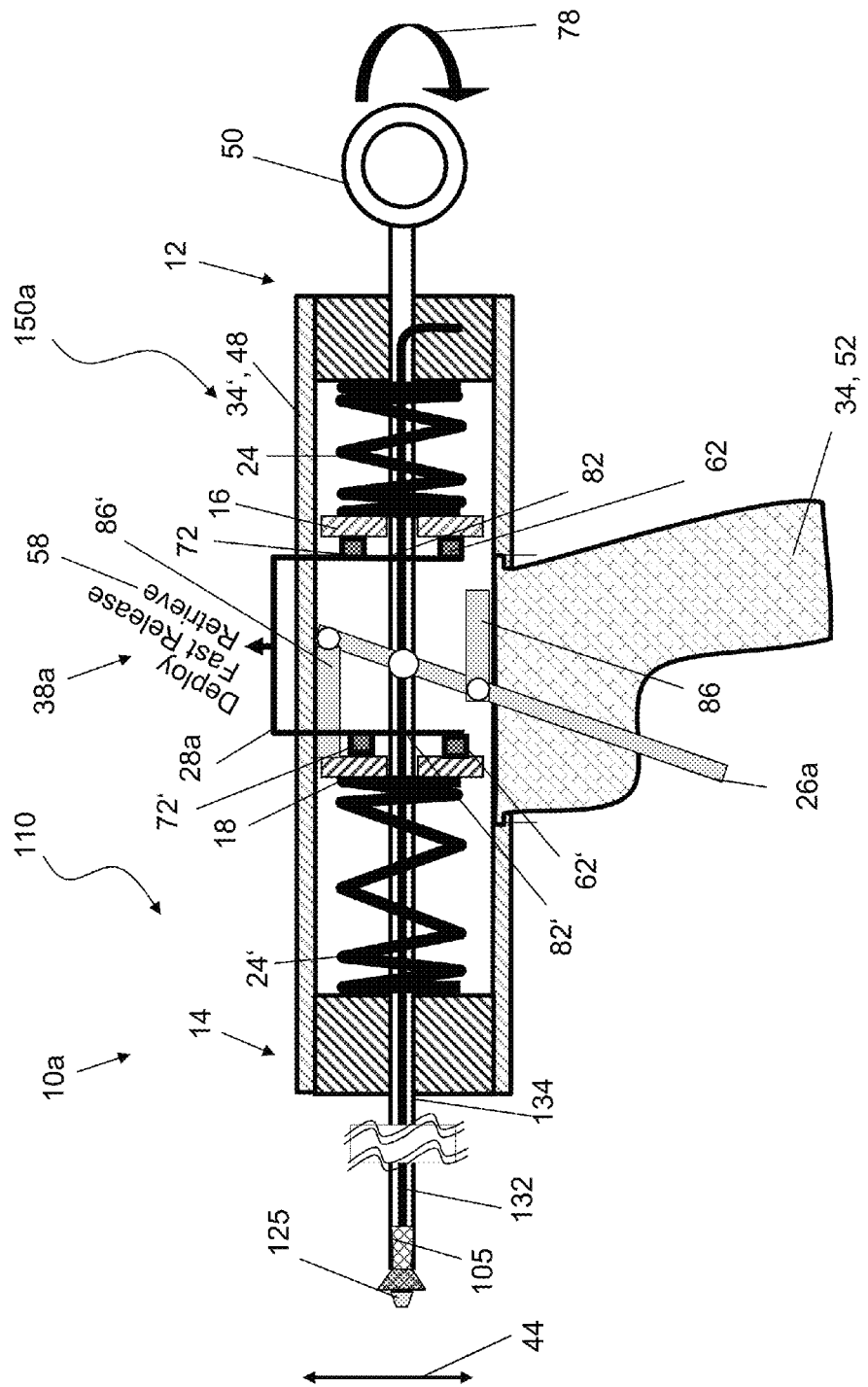
FIG. 12 shows the release device of FIG. 9 prepared for covering the implant.
Figure 13:
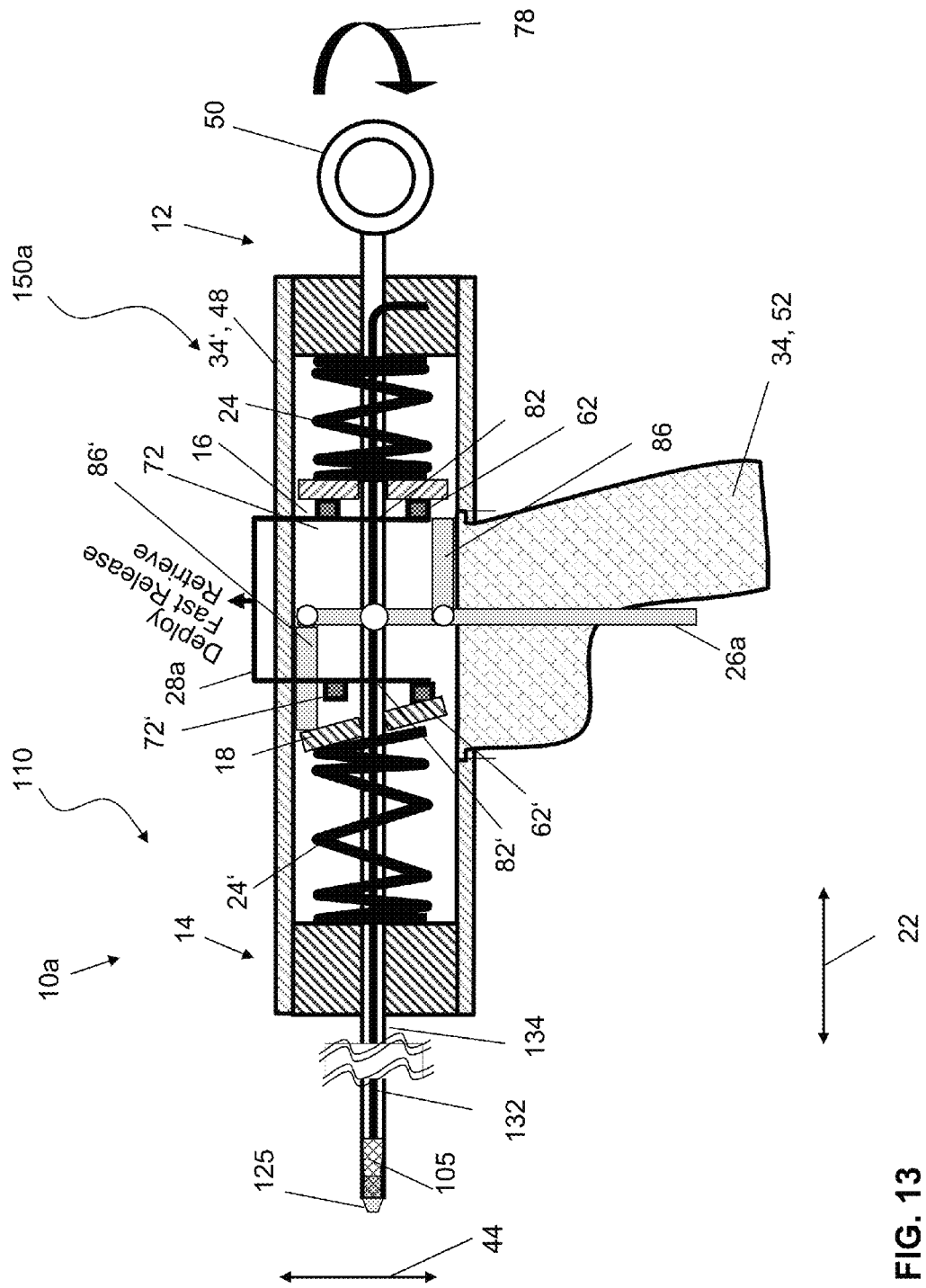
FIG. 13 shows the release device of FIG. 9 during covering of the implant.

Hereafter, the operating mode of covering the implant 105 with the outer insertion element 134, which is to say a retrieval mode, will be described based on FIGS. 12 and 13. The retrieval mode is activated by an axial displacement of the manipulating element 28*a* or of the selector switch in the direction of the proximal end 12. This is indicated to a user by an arrow directed to the lettering 58 "RETRIEVE". The stops 62, 72 of the limb 82 are axially displaced in the housing 48 such that the first actuator 16 is displaced in the direction of the proximal end 12 so far that, during counterclockwise actuation, the lower web 86 of the operating element 26*a* can no longer establish contact with the first actuator 16 (see FIG. 13). The stops 62', 72' of the limb 82' for the further actuator 18 are likewise displaced in the direction of the proximal end 12. As a result, the upper web 86' of the operating element 26*a* makes contact with the further actuator 18, tilts the same clockwise and thus cants the same on the outer insertion element 134 (see FIG. 12).

If the operating element 26*a* is now actuated counterclockwise, the upper web 86' shifts the canted actuator 18 in the direction of the distal end 14 and the actuator 18 carries the insertion element 134 in the direction of the distal end 14, again by way of a non-positive connection between the further actuator 18 and the outer insertion element 134. Due to the tilting movement of the further actuator 18 or the non-positive connection, a targeted relative movement is induced in the longitudinal direction 22 between the first and second insertion elements 132, 134. At a catheter tip 125, this results in an advancement of the outer insertion element 134 toward the catheter tip 125. If the implant 105 is axially blocked by the inner insertion element 132, the outer insertion element 134 again slides back in the direction of the distal end 14 over the implant 105 and covers the same. If the operating element 26*a* is released, a spring element 24', which is designed as a return spring, pushes the further actuator 18 into the non-canted upright position, or the position perpendicular relative to the outer insertion element 134 and back against the stops 62', 72'.

Figure 14:
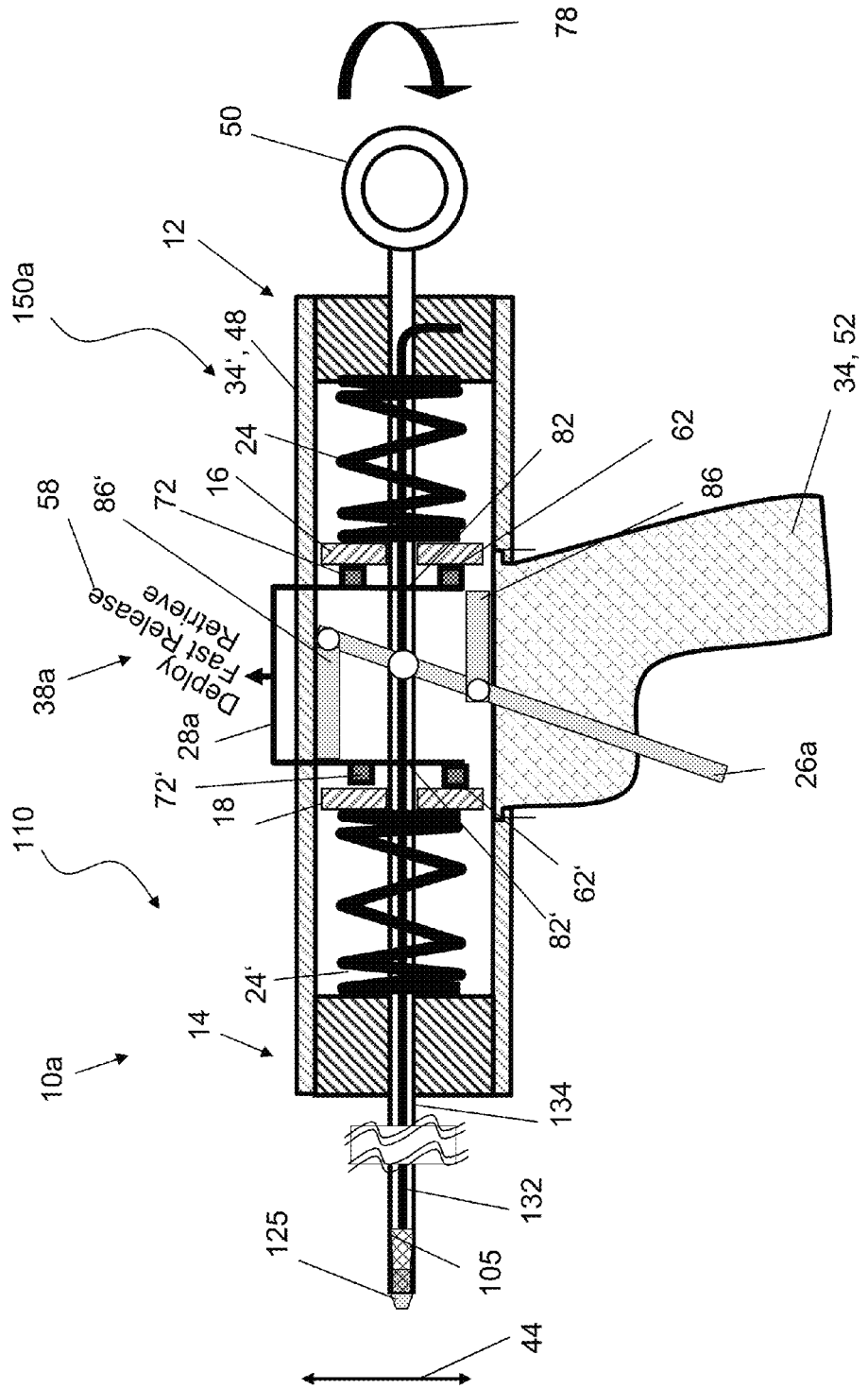
FIG. 14 shows the release device of FIG. 9 prepared for a fast release of the implant.
Figure 15:
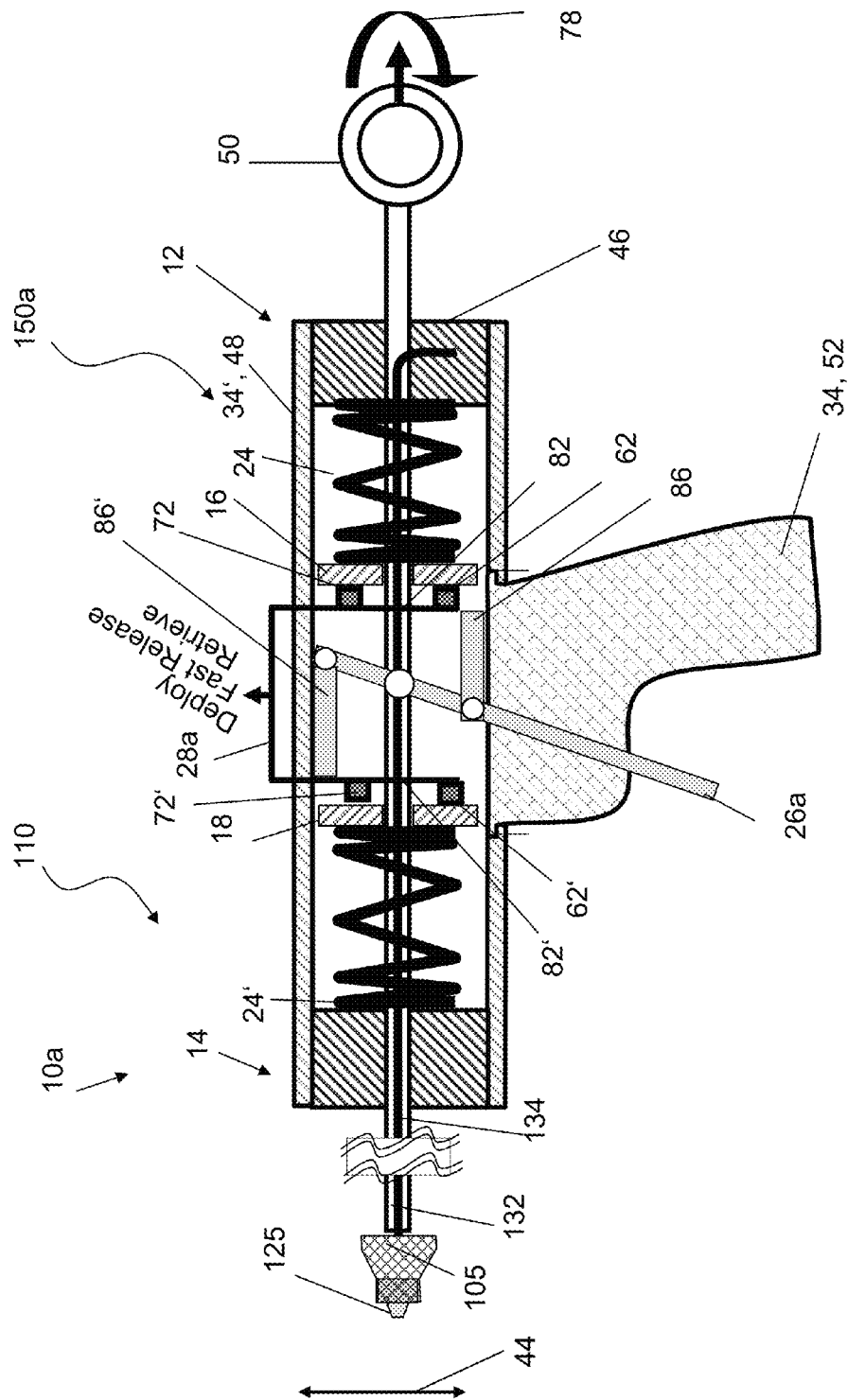
FIG. 15 shows the release device of FIG. 9 during the fast release of the implant.

FIGS. 14 and 15 show a third operating mode for a fast release of the implant 105, a fast release mode. The fast release mode is activated by axially displacing the manipulating element 28*a* into an axially central position. This is indicated to a user by an arrow directed to the lettering 58 "FAST RELEASE" (see FIG. 14). The stops 62, 62', 72, 72' of the limbs 82, 82' are displaced axially in the housing 48 such that the first and further actuators 16, 18 are displaced into axial central positions, so that the lower and upper webs 86, 86' of the operating element 26*a*, when not actuated, can no longer establish contact with these two (see FIG. 14). As a result, both actuators 16, 18 are disposed in a perpendicular position relative to the outer insertion element 134, whereby the non-positive connection is removed and the outer insertion element 134 can be moved freely. When the actuators 16, 18 are in the perpendicular position, the user can now pull on an operating element 50 at the proximal end of the outer insertion device 134 for a fast release of the implant 105. This moves the outer insertion element 134 in the direction of the proximal end 12 and the implant 105 is released (see FIG. 15).

FIGS. 16 to 20 show a second alternative embodiment of the body 10 and the release device 150 of FIGS. 1 to 9. The release device 150*b* or the body 10*b* of FIGS. 16 to 20 differs from the body 10 and the release device 150 of FIGS. 1 to 9 in that the body 10*b* comprises an alternative actuator 16. The, actuator 16 is embodied as a center part 90 of a tubular element 92 (see FIGS. 16 and 17). The tubular element 92 is arranged in a circumferential direction 78 of the body 10*b* around a circumference of an outer insertion element 134. Moreover, the tubular element 92 comprises two end parts 94, 94'; one at an end of the tubular element 92 arranged towards a proximal end 12 of the body 10*b* and the other at an end of the tubular element 92 arranged towards a distal end 14 of the body 10*b*. Each end part 94, 94' is connected to the center part 90 by an intermediate section 96, 96'.

The center part 90 and the end parts 94, 94' may have basically the same material thickness in a radial direction 44 of the tubular element 92. The intermediate sections 96, 96', in turn, have a reduced thickness compared to the center part 90 and the end parts 94, 94'. Hence, the intermediate sections 96, 96' have a reduced bending stiffness in comparison to the center part 90 and the end parts 94, 94'. The end parts 94, 94' are sliding elements to provide an easy sliding movement of the tubular element 92 on the outer insertion element 134. The center part 90, in turn, is provided to establish a non-positive connection between the tubular element 92 and the outer insertion element 134. The actuator 16 has a diameter $D_{16}$ which is selected such that the actuator 16 is disposed with play for a tilting movement of the actuator 16 relative to an inside diameter $D_{i10}$ of the body 10*b*.

The tubular element 92 and thus the actuator 16 is axially arranged between spring elements 24, 24' that both are designed as a pressure spring. One of the spring elements 24 extends between one end part 94 of the tubular element 92 and the proximal end 12 of the body 10*b* and the other spring element 24' between the other end part 94' of the tubular element 92 and the distal end 14 of the body 10*b*. Furthermore, the tubular element 92 is preloaded by each spring element 24, 24' and held in a middle position inside a housing 48 of the body 10*b*. In a starting configuration, which is set before implantation, for example, the actuator 16 is axially fixed in its respective axis 20 between the two spring elements 24, 24' (see FIGS. 16 and 19).

So as to effect a targeted relative movement in a longitudinal direction 22 or an axial direction between a first and the second insertion elements 132, 134 of the insertion device 110, the actuator 16 can be tilted about its axis 20 (see below). The axis 20 is oriented perpendicularly to the two insertion elements 132, 134.

In addition, the release device 150*b* comprises an operating element 26, which is formed by an operating lever. The operating element 26 is arranged in a clearance 98 of a manipulating element 28, embodied as a handle segment 34 or a pistol grip 52, and extends in its unbiased or non-actuated state basically in parallel to a rotational axis 32 of the manipulating element 28. Furthermore, the operating element 26 extends through an axially extending slot 100 in the housing 48 (see FIG. 17) to engage into a receptacle 102 of the actuator 16 or a receptacle 102 that is molded inside the actuator 16. Moreover, the operating element 26 is pivotably mounted about its installation point 56 in the receptacle 102 of the actuator 16. The installation point 56 is a pivot axis 84 of the operating element 26 that is oriented parallel to the axis 20 of the actuator 16 and lies at the same axial heights as the rotational axis 32 of the manipulating element 28 in the mode of the starting operation or with the tubular element 92 in its middle position. The release device 150b further comprises an indicator element 38 for indicating the set operating mode which is formed integrally with the manipulating element 28 or the pistol grip 52.

The actuator 16 can induce two different operating modes, and more specifically a release of an only schematically shown implant 105 and a covering of the implant 105 with the outer insertion element 134. The manipulating element 28 comprises an effective element 30 for changing between the two operating modes. This effective element 30 is formed by the clearance 98 for the operating element 26 in the manipulating element 28 and is disposed eccentrically to the rotational axis 32 of the manipulating element 28. Moreover, the operating element 26 is thus also arranged eccentrically in the clearance 98 of the manipulating element 28. In this position the tubular element 92 and thus the actuator 16 is positioned due to the unbiased or non-actuated operating element 26 in its middle position, where both spring elements 24, 24' are equally preloaded.

Figure 18:
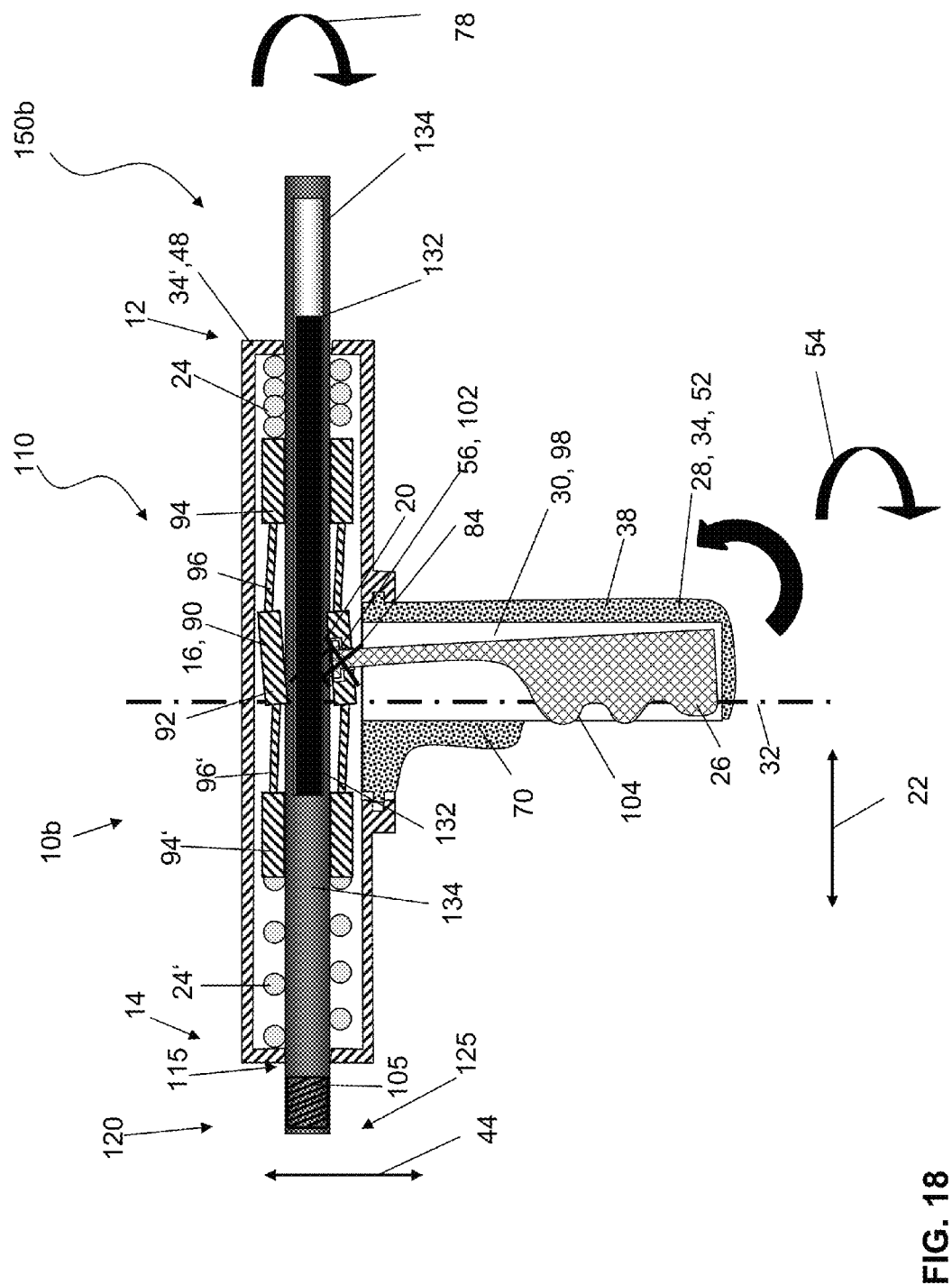
FIG. 18 shows the release device of FIG. 16 during the slow release of the implant.

A slow release of the implant 105 using a deploy mode will now be described based on FIGS. 16 and 18. To release the implant 105, the manipulating element 28 or the handle segment 34 (pistol grip 52) is positioned due to its rotation in the circumferential direction 54 so that a knob 70 of the handle segment 34 points in the direction of the distal end 14. Also an operating surface 104 of the operating element 26 points in direction of the distal end 14. So as to release the implant 105, this means that the exterior shaft is moved in the direction of the proximal end 12. In this arrangement, the tubular element 92 is in its middle position and tubular element 92 as well as the actuator 16 are arranged in parallel to the insertion elements 132, 134. In this position the spring elements 24, 24' are basically uncompressed.

By pivoting the operating element 26 in counterclockwise direction (see arrow) the actuator 16 is tilted around its axis 20 counterclockwise. This is enabled due to the reduced bending stiffness of the intermediate sections 96, 96' and thus a bending of the intermediate sections 96, 96' in clockwise direction. The actuator 16 thus effect a non-positive connection with the outer insertion element 134, whereby the same is axially fixed relative to the body 10b and the inner insertion element 132. If no further tilting is possible, the operating element 26 is subsequently shifted axially in direction of the proximal end 12 and the canted actuator 16 as well as the outer insertion element 134 is disposed axially displaceably parallel to the longitudinal direction 22 in direction of the proximal end 12. This will be possible till the spring element 24 is totally compressed, which limits the movement of the actuator 16 (see FIG. 18). By releasing the operating element 26 it will tilt back in its non-actuated position, thus also allowing the actuator 16 to tilt back in its non-canted parallel position in respect to the insertion elements 132, 134. Due to this, the non-positive connection between the actuator 16 and the outer insertion element 134 is removed. Hence, the spring element 24, which also constitutes a return spring, expands and the tubular element 92 is pushed back in the longitudinal direction 22 and in direction of the distal end 14, respectively, and in its middle or starting position.

The operating element 26 thus induces both the tilting movement and the targeted movement in the longitudinal direction 22 of the actuator 16 for the targeted relative movement in the longitudinal direction 22 between the first and second insertion elements 132, 134. Hence, the outer insertion element 134 uncovers the implant 105 that will expand automatically. This process can be repeated until the outer insertion element 134 completely exposes the implant 105. The release device 150b or the interior shaft is then retracted in the exterior shaft, and the insertion device 110 is removed from the body. The implant 105 remains fully positioned in the body (not shown).

Figure 19:
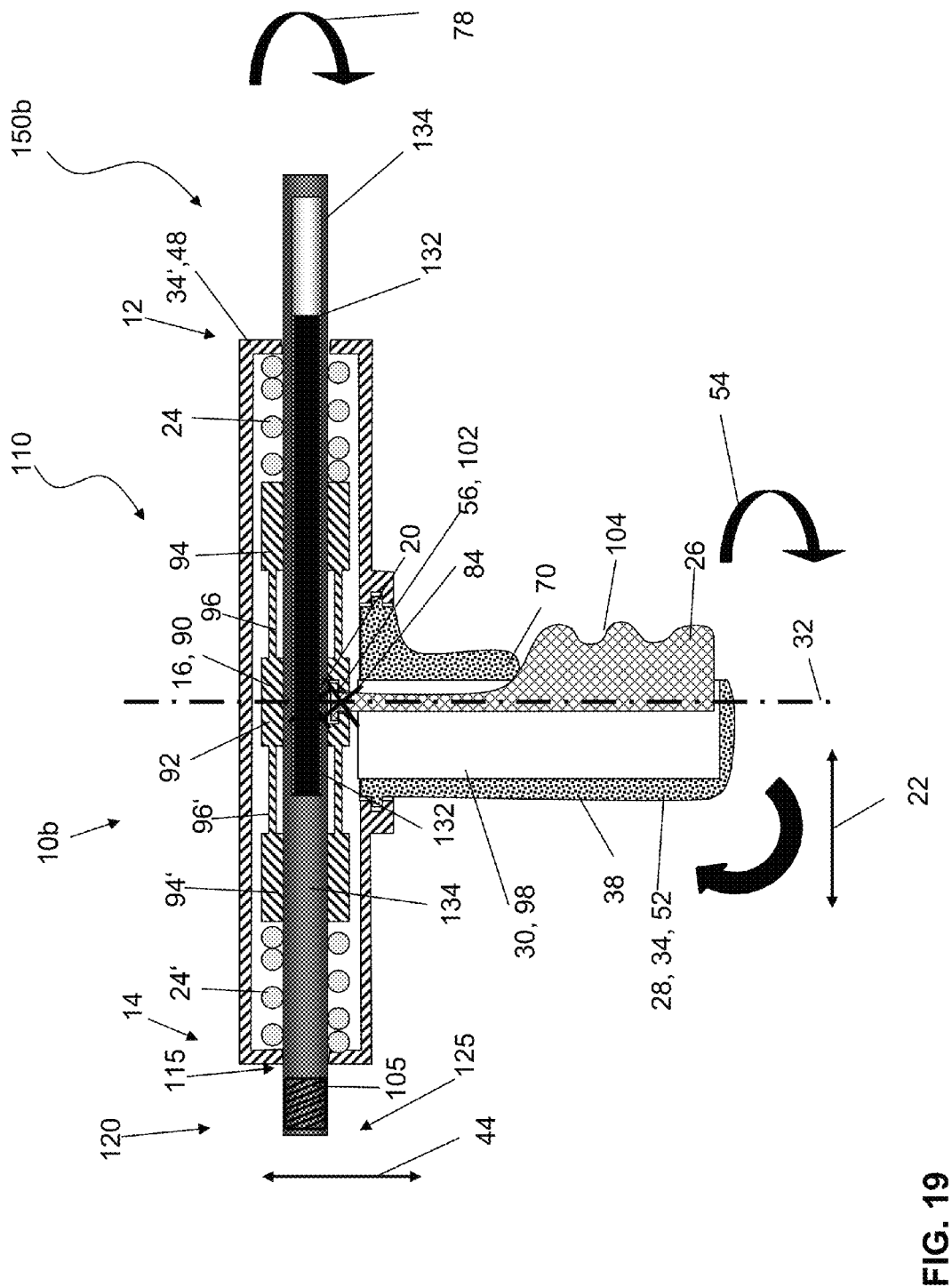
FIG. 19 shows the release device of FIG. 16 prepared for covering the implant.
Figure 20:
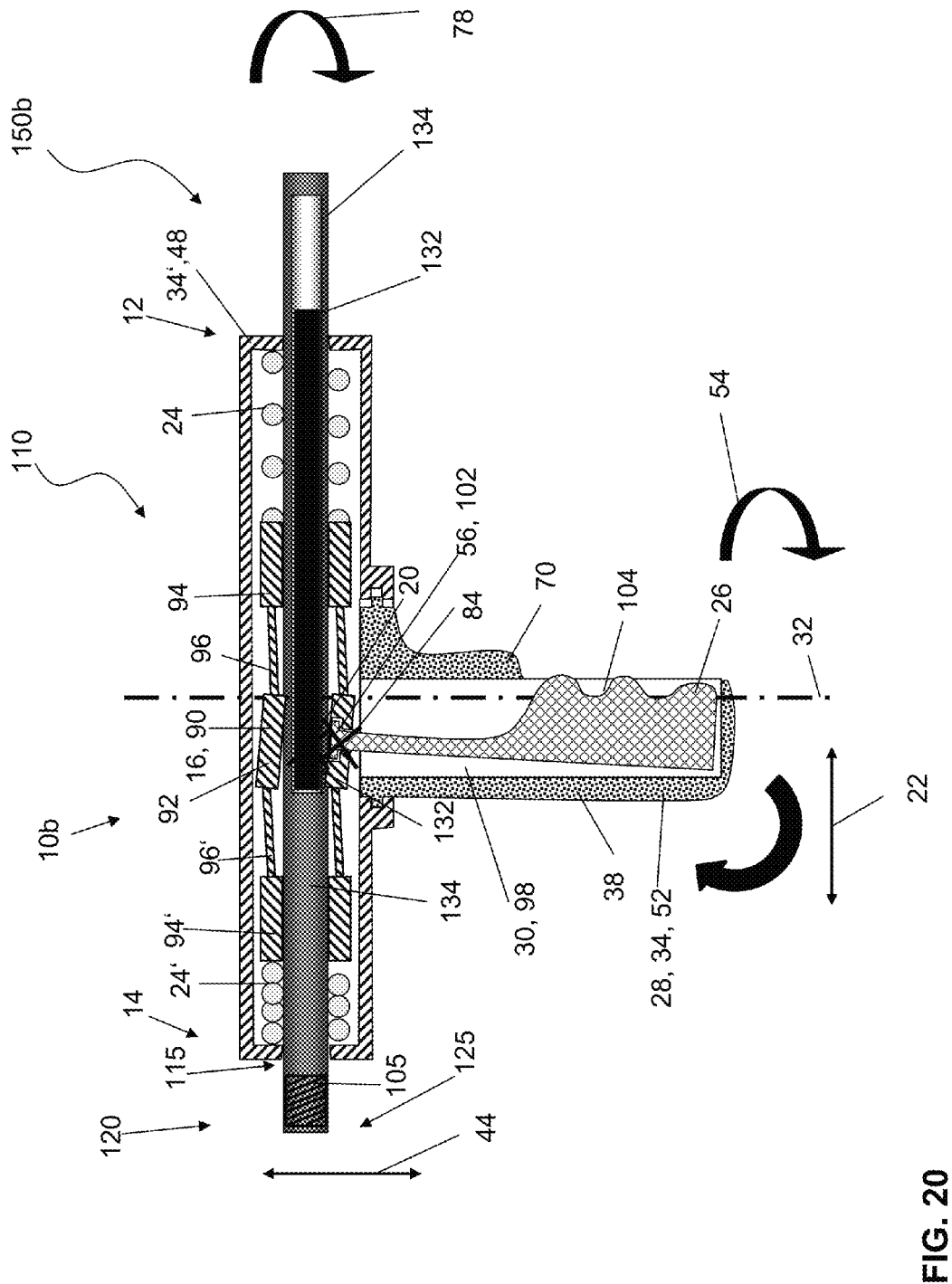
FIG. 20 shows the release device of FIG. 16 during covering of the implant.

Based on FIGS. 19 and 20, the operating mode of covering the implant 105 with the outer insertion element 134 is described, a retrieval mode. The retrieval mode is set by rotating the manipulating element 28 or the handle segment 34 (pistol grip 52) in the circumferential direction 54, so that the knob 70 of the handle segment 34 and the operating surface 104 of the operating element 26 point in the direction of the proximal end 12. In this arrangement, the tubular element 92 is in its middle position and the tubular element 92 as well as the actuator 16 are arranged in parallel to the insertion elements 132, 134. In this position the spring elements 24, 24' are basically uncompressed.

If the operating element 26 is now actuated clockwise (see arrow) it tilts the actuator 16 also clockwise. If no further tilting is possible, the operating element 26 is subsequently shifted axially in direction of the distal end 14 and the canted actuator 16 is also moved in the longitudinal direction 22 toward the distal end 14 and the actuator 16 in turn carries the outer insertion element 134 along by way of the non-positive connection toward the distal end 14. This will be feasible till the spring element 24' is totally compressed, which limits the movement of the actuator 16 (see FIG. 20). At a catheter tip 125, this results in an advancement of the outer insertion element 134 toward the catheter tip 125. If the implant 105 is axially blocked by the inner insertion element 132, the outer insertion element 134 again slides over the implant 105 and covers the same.

If the operating element 26 is now released, it will tilt back in its non-actuated position. This also allows the actuator 16 to tilt back in its non-canted parallel position in respect to the insertion elements 132, 134. Consequently, the non-positive connection between the actuator 16 and the outer insertion element 134 is removed. Subsequently, the spring element 24', which also constitutes a return spring, pushes the tubular element 92 in the longitudinal direction 22 in direction of the proximal end 12 and back to the middle or starting position. This process can be repeated until the outer insertion element 134 again completely covers the implant 105. The implant 105 is thus positioned in the outer insertion element 134 and the mounting is complete.

Figure 16:
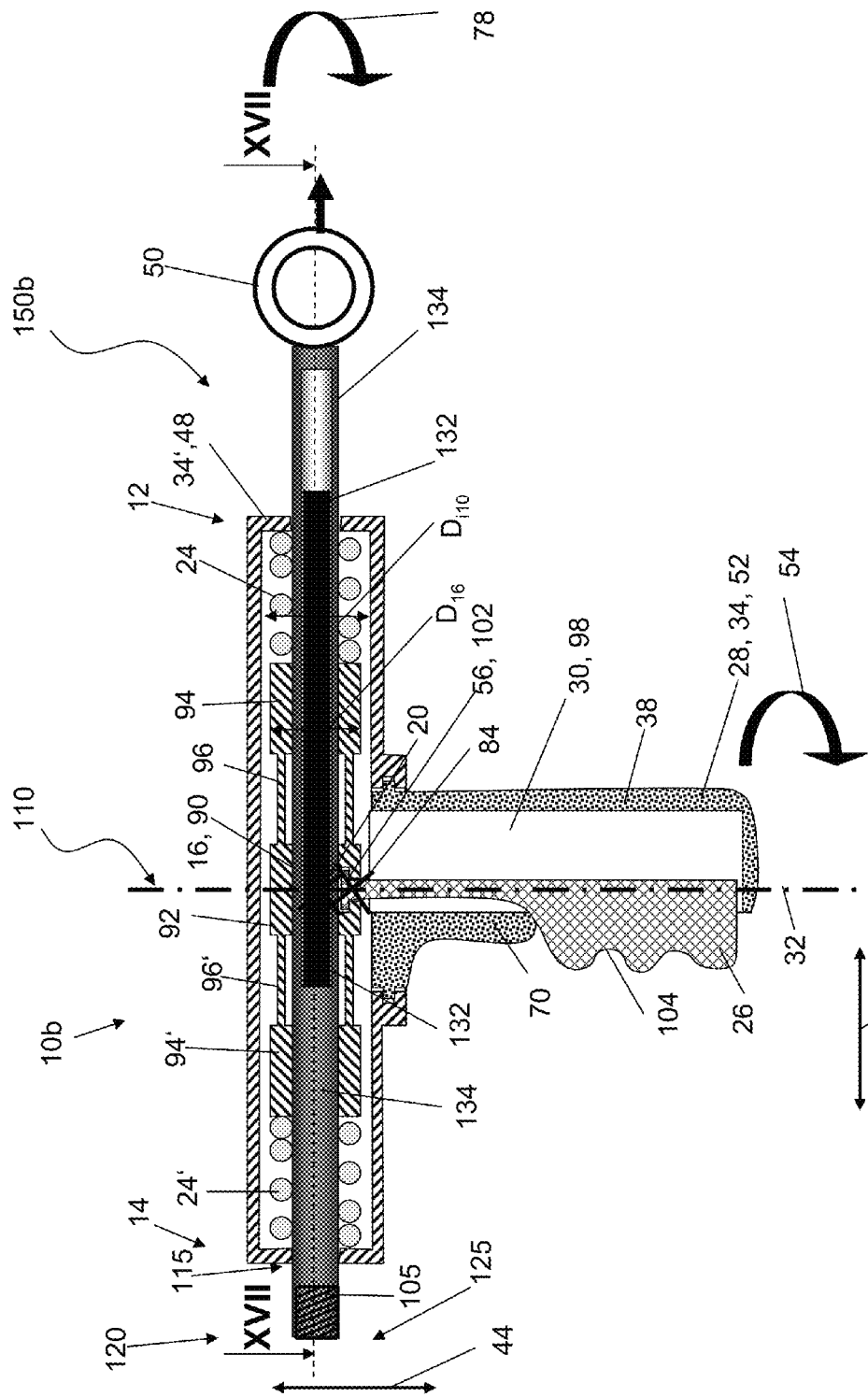
FIG. 16 is a second alternative release device prepared for a slow release of an implant.
Figure 17:
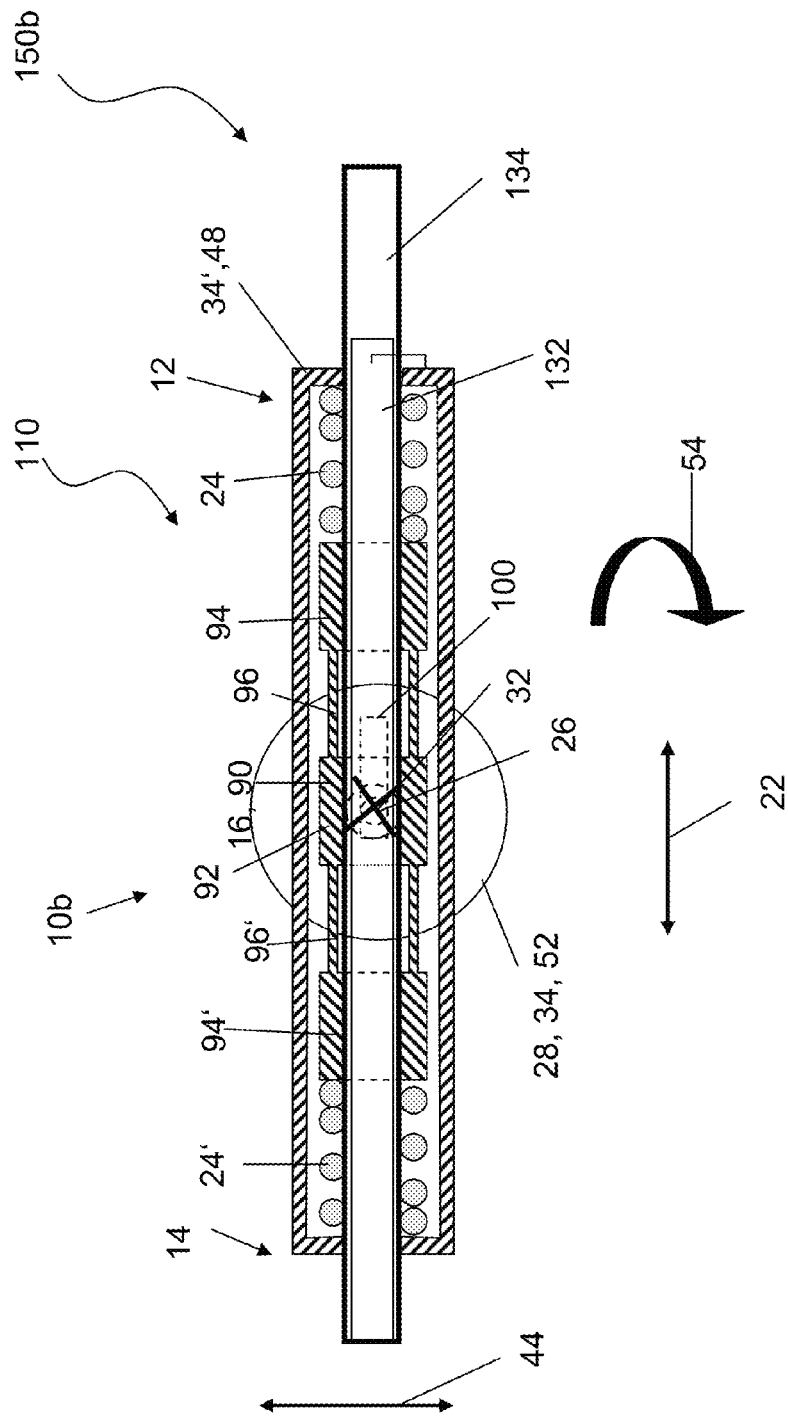
FIG. 17 shows a top view of the release device according to the indicated direction in FIG. 16.

A third operating mode for a fast release of the implant 105, a fast release mode may be actuated when the tubular element 92 is in its middle position (see FIGS. 16 and 19). There the actuator 16 is with the non-canted position relative to the outer insertion element 134, so that the outer insertion element 134 can be moved freely. When the actuator 16 is in this position, the user can now pull on an operating element 50 at the proximal end of the outer insertion device 134 for a fast release of the implant 105 (see arrow FIG. 16). This moves the outer insertion element 134 in the direction of the proximal end 12 and the implant 105 is released (not shown in detail).

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

REFERENCE NUMERALS

10 Body
12 End
14 End
16 Actuator
18 Actuator
20 Axis
22 Longitudinal direction
24 Spring element
26 Operating element
28 Manipulating element
30 Effective element
32 Rotational axis
34 Handle segment
36 Receptacle
38 Indicator element
40 Passage
42 Passage
44 Radial direction
46 Anchoring
48 Housing
50 Operating element
52 Pistol grip
54 Circumferential direction
56 Installation point
58 Lettering
60 Display
62 Stop
64 Region
66 Disk
68 Window
70 Knob
72 Stop
74 Plate
76 Pressure switch
78 Circumferential direction
80 Support surface
82 Limb
84 Pivot axis
86 Web
88 Inner wall
90 Center part
92 Element
94 End
96 Section
98 Clearance
100 Slot
102 Receptacle
104 Surface
105 Implant
110 Insertion device
115 End
120 End
125 Catheter tip
130 Shaft region
132 Insertion element
134 Insertion element
136 Outer sheath
150 Release device
D Diameter
$D_i$ Inside diameter

What is claimed is:

1. A release device for detaching a medical implant held between inner and outer insertion elements of an insertion device, the release device comprising:
   a body having a proximal end and a distal end;
   a first actuator positioned between the proximal and distal ends, wherein the first actuator can be tilted about an axis substantially perpendicularly to at least one of the insertion elements in a first direction so as to effect a targeted longitudinal movement of the outer insertion element in relation to the inner insertion element to release the implant;
   a further actuator that can be tilted in the first direction from the axis substantially perpendicular to the at least one of the insertion elements so as to cover the implant with the outer insertion element; and
   a manipulating element that selects between proximal and distal movement of the outer insertion element, wherein the manipulating element comprises two limbs, each limb comprising two stops that limit movement of the two actuators.

2. The release device according to claim 1, wherein the longitudinal movement occurs at least by means of a non-positive connection between the first actuator and the outer insertion element.

3. The release device according to claim 1, wherein the first actuator is preloaded by at least one spring element, wherein the first actuator can be returned to a starting position thereof by the at least one spring element.

4. The release device according to claim 1, further comprising an operating element to induce the tilting of the first actuator.

5. The release device according to claim 1, wherein the further actuator is provided between the proximal and distal ends of the body.

6. The release device according to claim 1, wherein the body further comprises a receptacle for the inner insertion element that immovably fixes the inner insertion element to the body during longitudinal movement of the outer insertion element.

7. The release device according to claim 1, wherein the body or the first actuator comprises at least one passage for at least one of the insertion elements.

8. The release device according to claim 1, wherein the device is configured to facilitate repositioning or retraction of a partially released implant.

* * * * *